US010675229B2

(12) United States Patent
Landa et al.

(10) Patent No.: US 10,675,229 B2
(45) Date of Patent: Jun. 9, 2020

(54) UV-PROTECTIVE COMPOSITIONS AND THEIR USE

(71) Applicant: LANDA LABS (2012) LTD., Rehovot (IL)

(72) Inventors: Benzion Landa, Nes Ziona (IL); Sagi Abramovich, Ra'anana (IL); Snir Dor, Petach Tikva (IL)

(73) Assignee: LANDA LABS (2012) LTD., Rehovot (IL)

( * ) Notice: Subject to any disclaimer, the term of this patent is extended or adjusted under 35 U.S.C. 154(b) by 0 days.

(21) Appl. No.: 15/714,723

(22) Filed: Sep. 25, 2017

(65) Prior Publication Data

US 2018/0055746 A1 Mar. 1, 2018

Related U.S. Application Data

(63) Continuation-in-part of application No. PCT/IB2016/051701, filed on Mar. 24, 2016.

(30) Foreign Application Priority Data

Mar. 24, 2015 (GB) .................................. 1504891.1
Mar. 24, 2015 (GB) .................................. 1504892.9
Mar. 24, 2015 (GB) .................................. 1504893.7
Mar. 24, 2015 (GB) .................................. 1504894.5

(51) Int. Cl.
*A61K 8/29* (2006.01)
*A61K 8/19* (2006.01)
*A61Q 17/04* (2006.01)
*C01G 31/00* (2006.01)
*A61K 8/27* (2006.01)
*C01G 29/00* (2006.01)
*C01G 23/00* (2006.01)
*C01G 9/02* (2006.01)
*C09D 7/61* (2018.01)
*A61K 8/02* (2006.01)
*A61K 8/81* (2006.01)
*C08K 9/02* (2006.01)
*C08K 3/24* (2006.01)
*C08K 3/22* (2006.01)

(52) U.S. Cl.
CPC .............. *A61K 8/29* (2013.01); *A61K 8/0241* (2013.01); *A61K 8/19* (2013.01); *A61K 8/27* (2013.01); *A61K 8/8147* (2013.01); *A61Q 17/04* (2013.01); *C01G 9/02* (2013.01); *C01G 23/006* (2013.01); *C01G 29/00* (2013.01); *C01G 31/00* (2013.01); *C09D 7/61* (2018.01); *A61K 2800/413* (2013.01); *C01P 2002/50* (2013.01); *C01P 2002/52* (2013.01); *C01P 2002/84* (2013.01); *C01P 2004/61* (2013.01); *C08K 3/22* (2013.01); *C08K 3/24* (2013.01); *C08K 9/02* (2013.01); *C08K 2201/011* (2013.01)

(58) Field of Classification Search
None
See application file for complete search history.

(56) References Cited

U.S. PATENT DOCUMENTS

| | | | |
|---|---|---|---|
| 5,260,403 A * | 11/1993 | Yamaguchi | ............ B41M 5/155 428/328 |
| 5,441,726 A | 8/1995 | Mitchnick et al. | |
| 5,614,310 A * | 3/1997 | Delgado | ............... A61F 13/023 428/316.6 |
| 6,015,655 A | 1/2000 | Hagemann et al. | |
| 6,197,282 B1 | 3/2001 | Oshima et al. | |
| 6,214,069 B1 * | 4/2001 | Blank | ................. C04B 35/1115 264/102 |
| 6,403,107 B1 | 6/2002 | Lemman | |
| 6,466,355 B1 | 10/2002 | Berneth et al. | |
| 9,144,536 B1 | 9/2015 | Daly et al. | |
| 2004/0039081 A1* | 2/2004 | Kawaguchi | .......... C09D 11/324 523/160 |
| 2004/0167008 A1* | 8/2004 | Hsu | ....................... B01F 17/005 501/82 |
| 2005/0249690 A1 | 11/2005 | Rojas-Wahl et al. | |
| 2010/0027192 A1 | 2/2010 | Perry et al. | |
| 2010/0092736 A1* | 4/2010 | Nishikawa | ........... B41M 5/0047 428/195.1 |
| 2010/0135937 A1 | 6/2010 | O'brien et al. | |
| 2011/0165269 A1 | 7/2011 | Khandar | |
| 2013/0171080 A1 | 7/2013 | Sarkar et al. | |

FOREIGN PATENT DOCUMENTS

| | | |
|---|---|---|
| CN | 102871942 | 1/2013 |
| DE | 102006035136 | 1/2008 |
| EP | 1000604 | 5/2000 |
| EP | 2061723 | 11/2009 |

(Continued)

OTHER PUBLICATIONS

Shen et al., Rheology of colloidal nanosized BaTiO3 suspension with ammonium salt of polyacrylic acid as a dispersant, Colloids and Surfaces A: Physicochem. Eng. Aspects 244 (2004) 61-66 (Year: 2004).*
International Search Report for PCT/IB2016/051701 dated Jun. 8, 2016.
Written Opinion for PCT/IB2016/051701 dated Jun. 8, 2016.
Reduction of the photocatalytic activity of ZnO nanoparticles for UV protection applications, Takuya Tsuzuki et al., International Journal of Nanotechnology. vol. 9. Issue Oct. 11, 2012. pp. 1017-1029 Inderscience Enterprises Ltd.
Machine Translation (by Google Patents) for CN 102871942 published on Jan. 16, 2013.
Machine Translation (by Google Patents) for DE 102006035136 published on Jan. 31, 2008.
Machine Translation (by EPO and Google) for JP 3441553 published on Oct. 8, 1999.

(Continued)

*Primary Examiner* — Jennifer A Berrios

(74) *Attorney, Agent, or Firm* — Daniel Feigelson; Fourth Dimension IP

(57) ABSTRACT

Disclosed are compositions comprising inorganic UV-absorbing agents and the use of such compositions, in particular for protecting a subject or the surface of an inanimate object against a harmful effect of ultraviolet radiation.

18 Claims, 18 Drawing Sheets

(56) References Cited

FOREIGN PATENT DOCUMENTS

| | | |
|---|---|---|
| EP | 2813264 | 12/2014 |
| EP | 2947050 | 11/2015 |
| GB | 2431103 | 4/2007 |
| JP | H08310913 | 11/1996 |
| JP | H09100112 | 4/1997 |
| JP | 3441553 | 10/1999 |
| JP | 2001002529 A | 1/2001 |
| JP | H08259425 | 9/2003 |
| JP | 2010090001 | 4/2010 |
| JP | 2014/088494 | 5/2014 |
| JP | 2014076923 A | 5/2014 |
| WO | WO 1994/024998 | 11/1994 |
| WO | 97/45097 | 12/1997 |
| WO | WO 2005/072680 | 8/2005 |
| WO | WO 2010/098249 | 9/2010 |

OTHER PUBLICATIONS

Machine Translation (by PlatPat) for JP H08310913 published on Nov. 26, 1996.
Machine Translation (by EPO and Google) for JP H08259425 published on Sep. 2, 2003.
Machine Translation (by EPO and Google) for JP 2001002529 published on Jan. 9, 2001.
Machine Translation (by PlatPat ) for JP 2010090001 published on Apr. 22, 2010.
Machine Translation (by Google Patents) for WO 2010/098249 published on Sep. 2, 2010.
U.S. Pat. No. 6,403,107 counterpart of EP1000604 published on May 17, 2000.
JP2014076923 Machine Translation (by EPO); original non-English document published on May 1, 2014.

\* cited by examiner

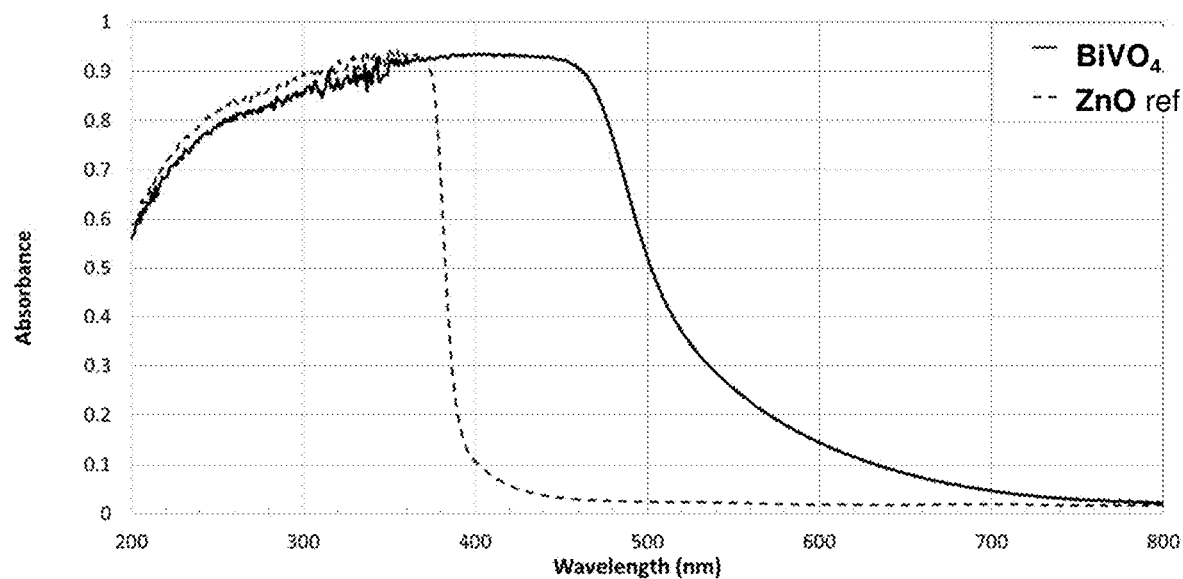
FIG. 1C
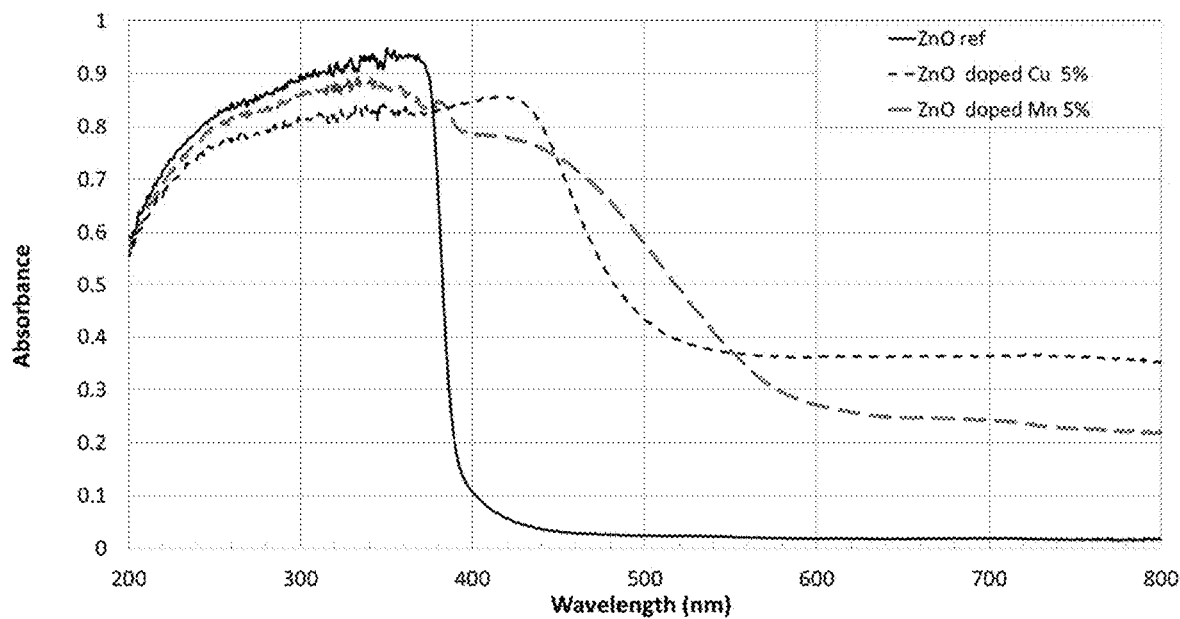
FIG. 1D-A

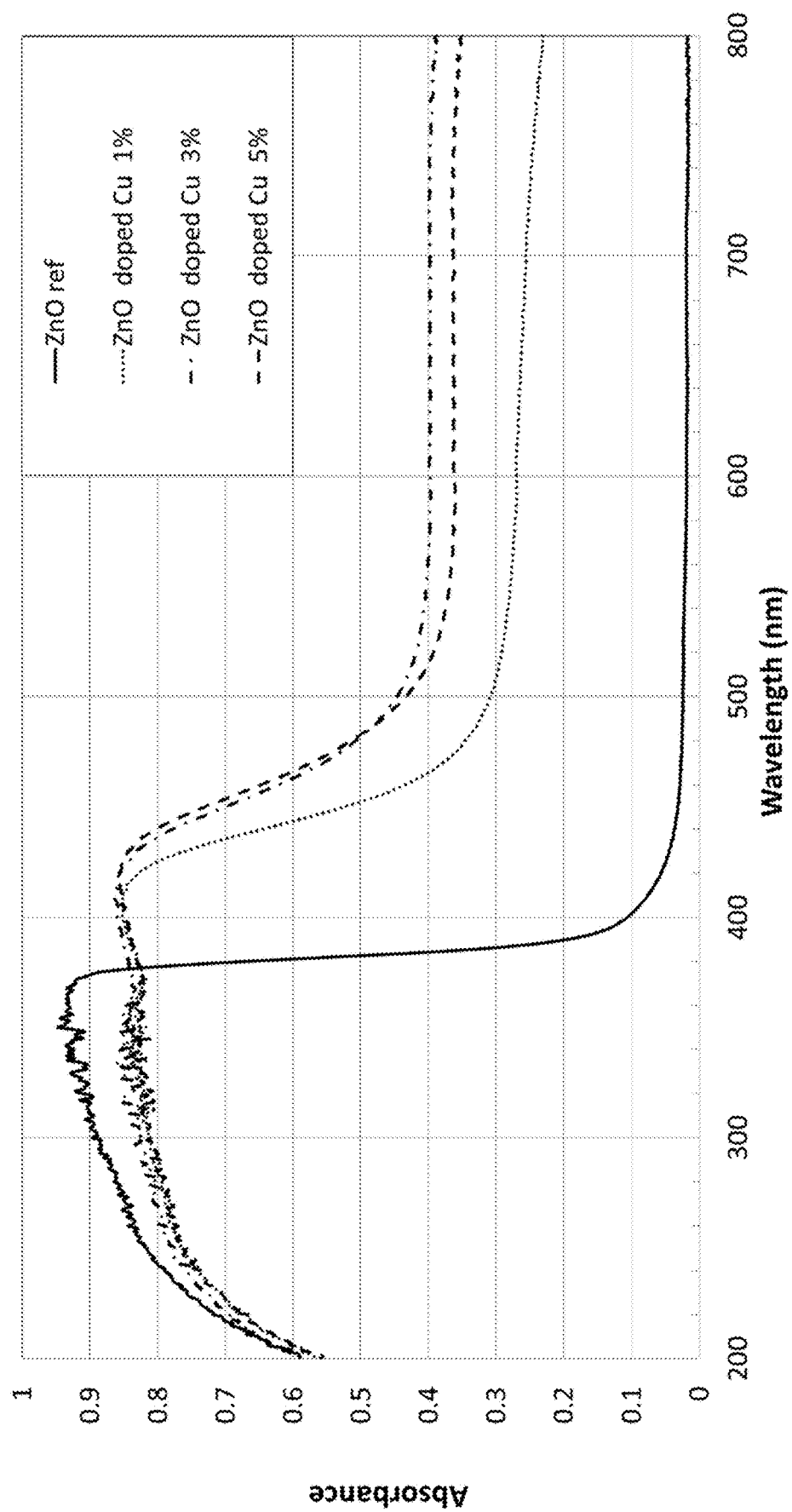
FIG. 1D-B

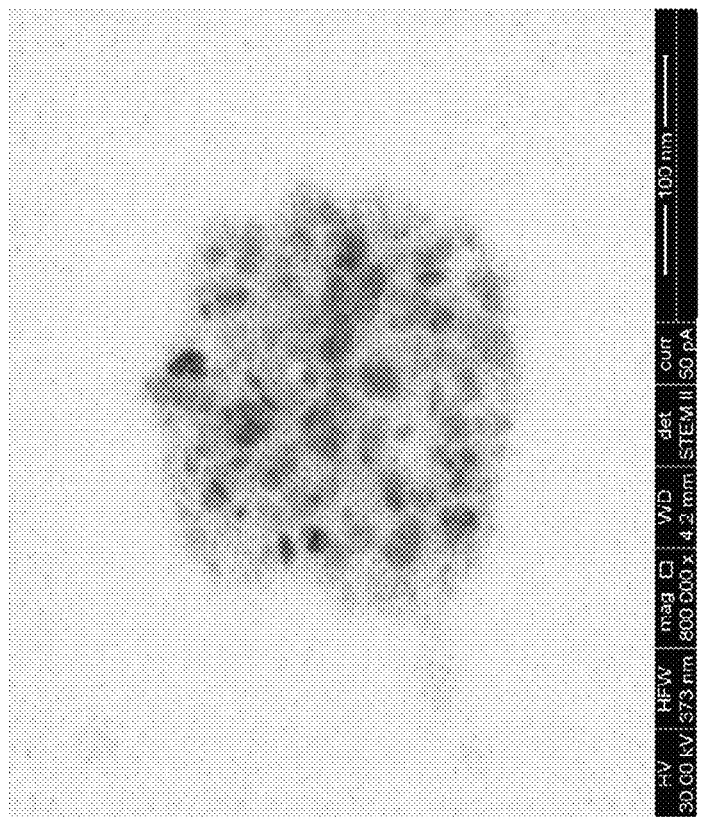
FIG. 3A-B
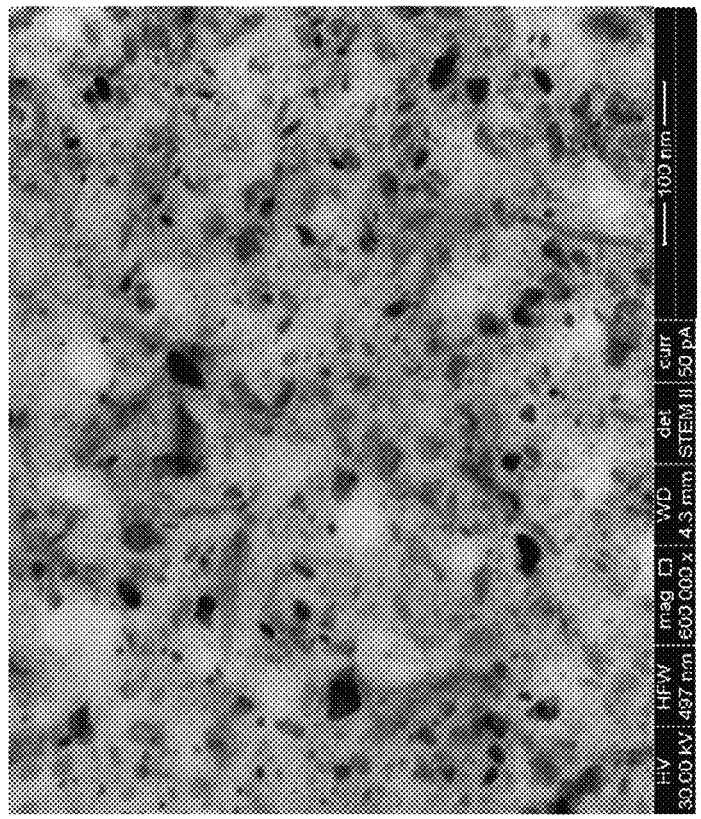
FIG. 3A-A

FIG. 3B-B
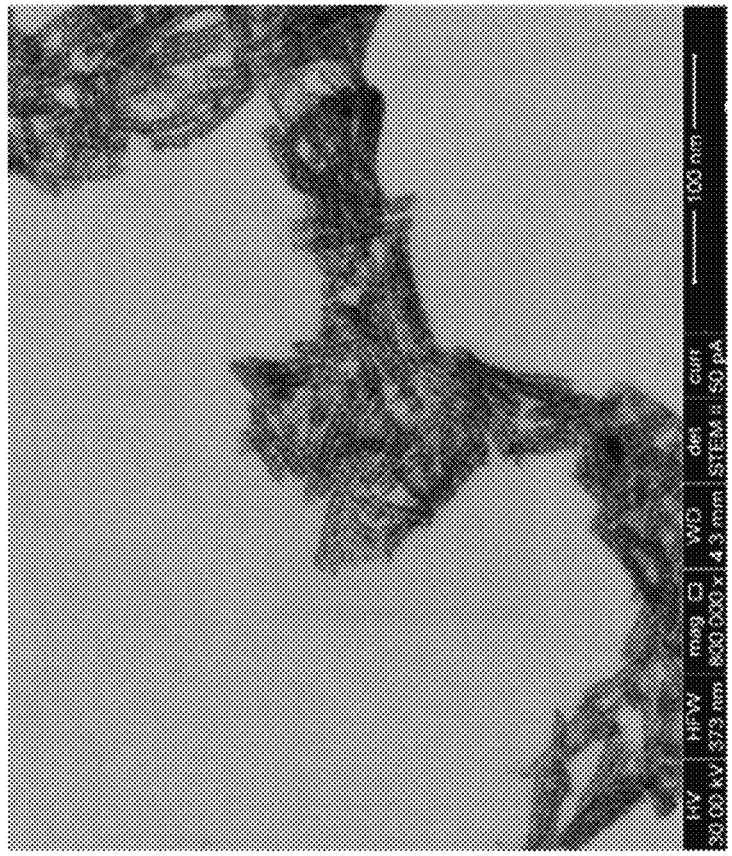
FIG. 3B-A

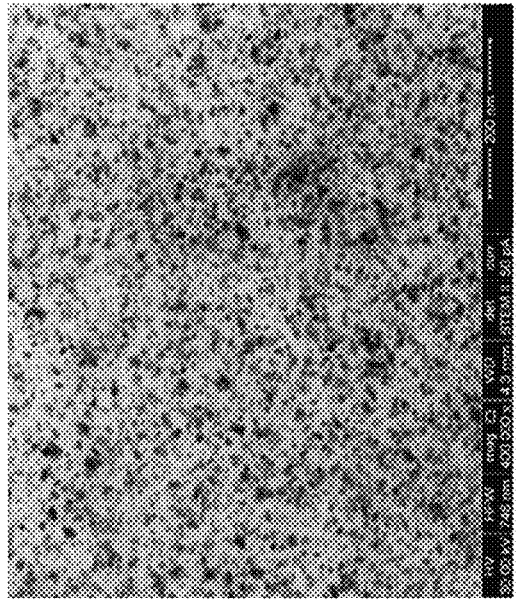
FIG. 3D-B
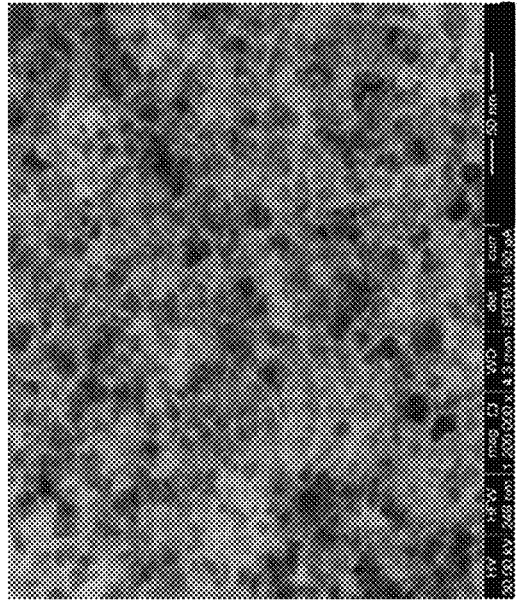
FIG. 3D-D
FIG. 3D-A
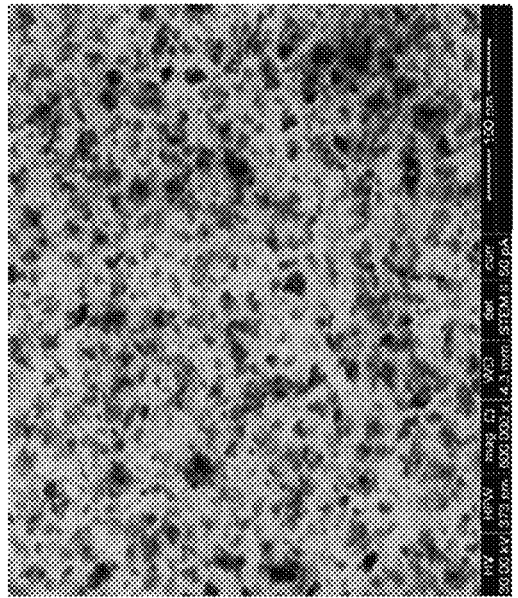
FIG. 3D-C

FIG. 4D-A

FIG. 4D-B
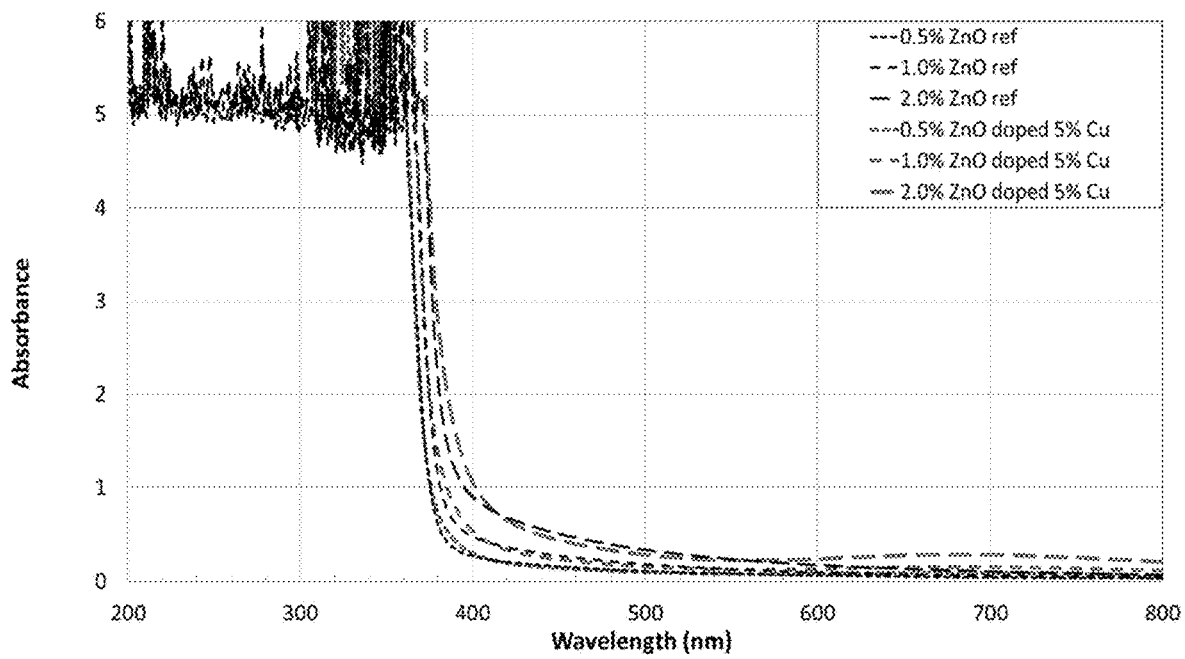
FIG. 4D-C
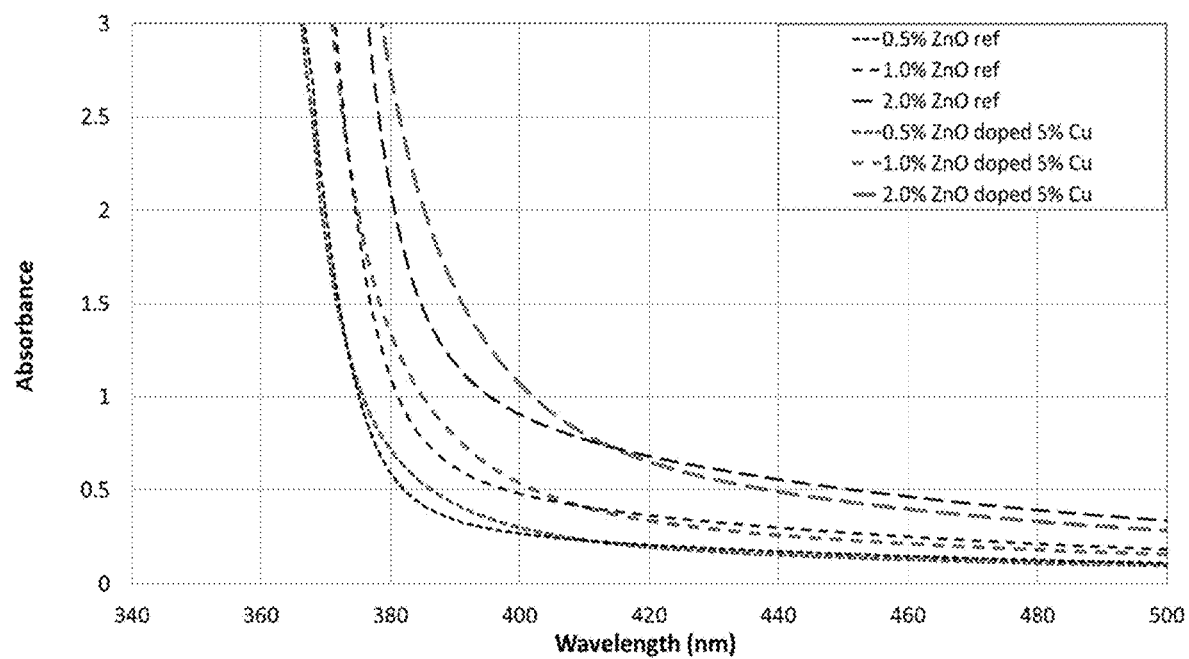

UV-PROTECTIVE COMPOSITIONS AND THEIR USE

CROSS-REFERENCE TO RELATED APPLICATIONS

This application is a Continuation-In-Part (CIP) of International Application No. PCT/IB2016/051701, filed Mar. 24, 2016, which claims priority from the following patent applications, all of which were filed Mar. 24, 2015: GB1504891.1; GB1504892.9; GB1504893.7; and GB1504894.5. All of the aforementioned applications are incorporated herein by reference for all purposes as if fully set forth herein.

FIELD

The present disclosure relates compositions that provide protection from ultraviolet radiation and to their use.

BACKGROUND

Ultraviolet (UV) radiation is ubiquitous, the sun being the most common source of UV radiation although not the only source. As UV radiation can cause damage to people, animals and objects, compositions that provide protection from UV radiation are useful.

In the biological context, UV-protective compositions, i.e. compositions that reduce or block the transmission of UV rays, are commonly employed to protect against sunburn. Sunburn is a form of radiation burn resulting from an overexposure to UV radiation, typically from the sun, but also from artificial sources, such as tanning lamps, welding arcs, and ultraviolet germicidal irradiation. Normal symptoms of sunburn in humans and other animals include reddening of the skin, general fatigue and mild dizziness. An excess of UV radiation can be life-threatening in extreme cases. Excessive UV radiation is considered to be the leading cause of non-malignant skin tumors, as well as increasing the risk of certain types of skin cancer.

Sunscreen compositions are commonly used to prevent sunburn and are believed to prevent squamous cell carcinomas and melanomas. Furthermore, they have been reported to delay the development of wrinkles and additional age-related skin conditions.

Specifically, sunscreen compositions are topical compositions that include components that absorb and/or reflect at least some of the sun's UV radiation on areas of skin exposed to sunlight, and thus reduce the effect of UV radiation on the skin. Depending on their mode of action, they are typically classified as chemical or physical sunscreens.

Chemical sunscreen compositions comprise organic compounds that absorb UV radiation to reduce the amount of UV radiation that reaches the skin. Being transparent to visible light and thereby being invisible when applied to the skin, chemical sunscreen compositions are popular for use. However, some organic compounds used in chemical sunscreen compositions have been found to generate free radicals which can cause skin damage, irritation and accelerated aging of the skin. Furthermore, organic materials may be absorbed into the skin, resulting in long-term detrimental health effects. Chemical sunscreen compositions may require the addition of a photostabilizer.

Physical sunscreen compositions reflect and absorb UV radiation. Known physical sunscreen compositions comprise particles of inorganic materials, mainly titanium oxide and/or zinc oxide. In order to obtain absorption and/or reflection of ultraviolet radiation over the full UVA and UVB range, relatively large particles are used. Due to the large particle size, such sunscreen compositions are viscous and opaque and tend to leave a white cast on the skin.

Many sunscreen compositions protect against UV radiation in the 280-315 nm range (UVB radiation) that causes sunburn, but do not against UV radiation in the 315-400 nm range (UVA radiation), which does not primarily cause sunburn but can increase the rate of melanoma and photodermatitis.

It is generally preferred that sunscreen compositions, when applied to the skin, appear transparent to the eye. In order for physical sunscreen compositions to appear transparent to the eye, the particles of inorganic material should be in the form of nanoparticles, which absorb and/or scatter UV light but not visible light, rendering them substantially transparent to the eye when applied on the skin. However, use of nanoparticles reduces the range of wavelengths absorbed by the inorganic materials. Some known sunscreen compositions therefore block both UVA and UVB radiation by use of a combination of different UV-absorbing or scattering materials, generally termed UV-protecting agents, each of which blocks radiation over a limited range of the UV spectrum.

Similarly, UV-protective compositions can benefit inert materials or objects that may be negatively affected by UV radiation. For instance, UV radiation can reduce the lifespan of materials (e.g., natural and synthetic polymers), and exposure to UV radiation may cause changes in colors of objects, especially in objects that are subjected to prolonged sun exposure, such as buildings or vehicles. Various coatings are known to achieve such protection. The provision of such coatings may in turn benefit health. For example, optical lenses having a UV-protective coating may reduce the transmission of such radiation to the eye, thus reducing UV-induced optical disorders such as cataract. Similarly, materials serving for the fabrication of windows that incorporate or are coated with suitable UV-protecting agents may reduce the transmission of such rays to subjects, plants or objects shielded by such windows.

SUMMARY

There is provided, in accordance with an aspect of the invention, a composition that when applied to a surface provides protection from UV radiation, i.e. a UV-protective composition, which comprises particles of at least one inorganic UV-absorbing agent selected from the group consisting of (i) barium titanate ($BaTiO_3$), (ii) bismuth oxide ($Bi_2O_3$), (iii) bismuth vanadate ($BiVO_4$), and (iv) doped zinc oxide (ZnO). In some embodiments, the inorganic UV-absorbing agent is barium titanate. In some embodiments, the inorganic UV-absorbing agent is bismuth oxide. In some embodiments, the inorganic UV-absorbing agent is bismuth vanadate. In some embodiments, the inorganic UV-absorbing agent is doped zinc oxide. In some embodiments, the composition contains a mixture of particles of two or more of the aforementioned inorganic UV-absorbing agents.

According to a further aspect of the invention, there is provided a UV-protective composition comprising nanoparticles of at least one inorganic UV-absorbing agent selected from the group consisting of (i) barium titanate ($BaTiO_3$) and (ii) bismuth vanadate ($BiVO_4$), wherein said inorganic UV-absorbing agent has a median particle diameter, on a particle number basis ($D_N50$), of at most 100 nm, or wherein at least 50% of the number of said nanoparticles of said at least one inorganic UV-absorbing agent have at least one dimension of at most 100 nm, and wherein a critical wavelength of said inorganic UV-absorbing agent is within a range of 330 to 400 nm.

According to yet a further aspect of the invention, there is provided a UV-protective composition comprising nanoparticles of at least one inorganic UV-absorbing agent selected from the group consisting of (i) barium titanate ($BaTiO_3$) and (ii) bismuth vanadate ($BiVO_4$), wherein said inorganic UV-absorbing agent has a median particle diameter, on a particle number basis ($D_N50$), of at most 100 nm, or wherein at least 50% of the number of said nanoparticles of said at least one inorganic UV-absorbing agent have at least one dimension of at most 100 nm, wherein a critical wavelength of said inorganic UV-absorbing agent is within a range of 330 to 400 nm, and wherein an area under the curve formed by UV-absorbance of a particular one of said inorganic UV-absorbing agent, as a function of wavelength in a range of 280 nm to 400 nm ($AUC_{280-400}$), is at least 60%, at least 65%, at least 70%, or at least 75% of the AUC formed by said particular one of said inorganic UV-absorbing agent, at the same concentration, in a range of 280 nm to 700 nm ($AUC_{280-700}$).

According to yet a further aspect of the invention, there is provided a UV-protective composition comprising nanoparticles of at least one inorganic UV-absorbing agent selected from the group consisting of (i) barium titanate ($BaTiO_3$) and (ii) bismuth vanadate ($BiVO_4$), wherein said inorganic UV-absorbing agent has a median particle diameter, on a particle number basis ($D_N50$), of at most 100 nm, or wherein at least 50% of the number of said nanoparticles of said at least one inorganic UV-absorbing agent have at least one dimension of at most 100 nm, wherein a critical wavelength of said inorganic UV-absorbing agent is within a range of 330 to 400 nm, wherein an area under the curve formed by UV-absorbance of a particular one of said inorganic UV-absorbing agent, as a function of wavelength in a range of 280 nm to 400 nm ($AUC_{280-400}$), is at least 60%, at least 65%, at least 70%, or at least 75% of the AUC formed by said particular one of said inorganic UV-absorbing agent, at the same concentration, in a range of 280 nm to 700 nm ($AUC_{280-700}$), and wherein an overall polydispersity index (PDI) of said inorganic UV-absorbing agent is within a range of 0.13 to 0.30.

As used herein in the specification and in the claims section that follows, the term "UV absorbance selectivity", with respect to a formulation or at least one UV-absorbing agent thereof, is defined as the ratio ($R_{AUC}$) of area under the curve (AUC), on a percentage basis, formed by (1) UV-absorbance by the formulation or inorganic UV-absorbing agent(s), over a wavelength range of 280 nm to 400 nm ($AUC_{280-400}$), divided by (2) the AUC formed by the identical formulation or inorganic UV-absorbing agent(s), at the identical concentration, and over a wavelength range of 280 nm to 700 nm ($AUC_{280-700}$):

$$(R_{AUC}) = 100\% \cdot (AUC_{280-400})/(AUC_{280-700})$$

Absorbance, for determining the "UV absorbance selectivity", is measured using a Cary 300 UV-Vis spectrophotometer (or substantially identical, as will be known to those skilled in the art) with quartz cuvette (10 mm light pathway), without any type of integrated sphere unit.

Typically, a 2% suspension is used to evaluate the UV absorbance selectivity.

In some embodiments, the $R_{AUC}$ of the barium titanate is at least 75%, at least 80%, at least 82%, at least 85%, at least 87%, at least 90%, or at least 92%, and optionally, at most 99%, at most 98%, at most 97%, at most 96%, at most 95%, at most 94%, or at most 93%.

In some embodiments, the $R_{AUC}$ of the barium titanate is within a range of 75% to 99%, 80% to 99%, 82% to 99%, or 85% to 99%, more typically, within a range of 75% to 95%, 80% to 95%, 82% to 95%, or 85% to 95%, or within a range of 75% to 92%, 80% to 90%, 80% to 87%, 80% to 85%, 75% to 90%, 82% to 92%, 82% to 90%, or 82% to 87%.

In some embodiments, the $R_{AUC}$ of the bismuth vanadate is at least 60%, at least 65%, at least 67%, at least 70%, at least 72%, at least 75%, at least 77%, at least 80%, at least 82%, at least 85%, at least 87%, or at least 90%, and optionally, at most 95%, at most 93%, at most 92%, or at most 91%.

In some embodiments, the $R_{AUC}$ of the bismuth vanadate is within a range of 60% to 95%, 65% to 95%, 70% to 95%, 75% to 95%, 80% to 95%, or 85% to 99%, more typically, within a range of 70% to 90%, 75% to 90%, 77% to 90%, or 80% to 90%, or within a range of 75% to 92%, 77% to 90%, 77% to 85%, 80% to 90%, 80% to 87%, 80% to 85%, 77% to 87%, 80% to 92%, 82% to 90%, or 82% to 87%.

In some embodiments, the UV-protective composition further comprises a neutralized polyacrylic acid (e.g., potassium or sodium base).

In some embodiments, the weight ratio of the dispersant (typically a neutralized polyacrylic acid (NPA)) to the inorganic UV-absorbing agent is within a range of 1:2.5 (1 part NPA to 2.5 parts inorganic UV-absorbing agent) to 2.5:1, 1:2 to 2.5:1, 1:2 to 2.0:1, 1:2 to 1.5:1, 1:2 to 1.3:1, 0.7:1 to 2.5:1, 0.8:1 to 2.5:1, 1:1 to 2.5:1, 1:1 to 2.0:1, 1.2:1 to 2.5:1, 1.2:1 to 2.0:1, or 0.8:1 to 1.2:1.

In some embodiments, at least a portion of the dispersant (e.g., NPA) is attached to, or at least partially envelops, said at least one inorganic UV-absorbing agent.

In some embodiments, the overall polydispersity index (PDI) of the barium titanate or the bismuth vanadate is within a range of 0.10 to 0.38, 0.10 to 0.35, 0.13 to 0.35, 0.13 to 0.32, 0.13 to 0.30, 0.13 to 0.27, 0.13 to 0.25, 0.13 to 0.25, 0.13 to 0.25, and optionally, at least 0.15, at least 0.17, or at least 0.2.

As used herein in the specification and in the claims section that follows, the polydispersity index (PDI), which is based on dynamic light scattering (DLS) data, is calculated according the ISO standard document 13321:1996 E and ISO 22412:2008 (e.g., as described in the Malvern Inform White Paper (© 2011 Malvern Instruments Limited). The polydispersity index is a dimensionless number calculated from a simple 2 parameter fit to the correlation data (the cumulants analysis). The Polydispersity Index is scaled such that values smaller than 0.05 are rarely seen other than with highly monodisperse standards. Values greater than 0.70 indicate that the sample has a very broad size distribution. The various size distribution algorithms work with data that falls between 0.05 and 0.70.

In some embodiments, the critical wavelength of the inorganic UV-absorbing agent (e.g., barium titanate) is at least 335 nm, at least 340 nm, at least 345 nm, at least 350 nm, at least 355 nm, at least 360 nm, at least 365 nm, or at least 370 nm.

In some embodiments, the inorganic UV-absorbing agent includes or consists essentially of said bismuth vanadate, wherein the critical wavelength of the bismuth vanadate is at least 380 nm, at least 385 nm, or at least 390 nm.

In some embodiments, the inorganic UV-absorbing agent has a $D_N50$ of at most 90 nm or at most 80 nm, and more typically, at most 75 nm, at most 70 nm, at most 65 nm, at most 60 nm, at most 55 nm, at most 50 nm, at most 45 nm, or at most 40 nm.

In some embodiments, the inorganic UV-absorbing agent has a $D_N50$ of at least 15 nm, at least 20 nm, at least 25 nm, at least 30 nm, or at least 35 nm.

In some embodiments, the inorganic UV-absorbing agent has a $D_N50$ within a range of 15 to 80 nm, 15 to 70 nm, 15 to 60 nm, 20 to 75 nm, 20 to 70 nm, 20 to 65 nm, 25 to 70 nm, 25 to 60 nm, 25 to 50 nm, 30 to 65 nm, 30 to 60 nm, 30 to 55 nm, or 30 to 50 nm.

In some embodiments, the composition is formulated as a sunscreen composition for application to human skin or, additionally or alternatively, for application to non-human skin, i.e. animal skin. In some embodiments, the composition is formulated as a composition for application to hair, such as a shampoo or conditioner. In some embodiments, the composition is formulated for application to an inanimate surface, such as a varnish or lacquer.

In some embodiments, the inorganic UV-absorbing agent is present in the composition as nanoparticles having at least one dimension of up to about 100 nm.

In some embodiments, at least 50% of the number of inorganic UV-absorbing agent nanoparticles present in the composition has at least one dimension of up to about 100 nm.

In some embodiments, at least 50% of the volume of inorganic UV-absorbing agent nanoparticles present in the composition has at least one dimension of up to about 100 nm.

In some embodiments, at least 90% of the number of inorganic UV-absorbing agent nanoparticles present in the composition has at least one dimension of up to about 100 nm.

In some embodiments, at least 90% of the volume of inorganic UV-absorbing agent nanoparticles present in the composition has at least one dimension of up to about 100 nm.

In some embodiments, at least 95% of the number of inorganic UV-absorbing agent nanoparticles present in the composition has at least one dimension of up to about 100 nm.

In some embodiments, at least 95% of the volume of inorganic UV-absorbing agent nanoparticles present in the composition has at least one dimension of up to about 100 nm.

In some embodiments, at least 97.5% of the number of inorganic UV-absorbing agent nanoparticles present in the composition has at least one dimension of up to about 100 nm.

In some embodiments, at least 97.5% of the volume of inorganic UV-absorbing agent nanoparticles present in the composition has at least one dimension of up to about 100 nm.

In some embodiments, at least 99% of the number of inorganic UV-absorbing agent nanoparticles present in the composition has at least one dimension of up to about 100 nm.

In some embodiments, at least 99% of the volume of inorganic UV-absorbing agent nanoparticles present in the composition has at least one dimension of up to about 100 nm.

In some embodiments, the sunscreen composition comprising the inorganic UV-absorbing agent is devoid of an organic ultraviolet-absorbing agent.

In some embodiments, the inorganic UV-absorbing agent is the sole ultraviolet-absorbing agent in the composition.

In some embodiments, when the inorganic UV-absorbing agent is doped zinc oxide, (a) the doped zinc oxide is present as nanoparticles having at least one dimension of up to about 100 nm, (b) the doped zinc oxide comprises from about 90% or even from 95% to about 99.9% molar percentage zinc oxide and from about 0.1% to about 5% or even 10% molar percentage of a metal cation as a dopant, and (c) the composition is devoid of an organic ultraviolet-absorbing agent.

In some embodiments, UV-absorbing agent is present in the composition at a concentration in the range of from about 0.001% to about 40% (w/w) of the composition. In some embodiments, the inorganic UV-absorbing agent constitutes at least 0.01 wt. %, at least 0.1 wt. %, at least 0.5 wt. %, at least 1 wt. %, at least 2 wt. %, at least 3 wt. %, at least 4 wt. %, at least 5 wt. %, at least 10 wt. %, at least 15 wt. %, at least 20 wt. %, at least 25 wt. %, at least 30 wt. %, at least 35 wt. %, or at least 40 wt. %. of the composition. In some embodiments, the inorganic UV-absorbing agent constitutes at most 40 wt. %, at most 35 wt. %, at most 30 wt. %, at most 25 wt. %, at most 20 wt. %, at most 15 wt. %, at most 10 wt. %, at most 5 wt. %, at most 4 wt. %, at most 3 wt. %, at most 2 wt. %, at most 1 wt. %, at most 0.5 wt. %, or at most 0.1 wt. % of the composition.

In some embodiments, the composition further comprises a metallic agent comprising silver particles. In some embodiments, the silver particles comprise silver nanoparticles having at least one dimension of up to about 50 nm. In some embodiments, at least 95% of the number of silver nanoparticles present in the composition has at least one dimension of up to about 50 nm. In some embodiments, at least 95% of the volume of silver nanoparticles present in the composition has at least one dimension of up to about 50 nm. In some embodiments, wherein the composition comprises silver nanoparticles, the composition is devoid of an additional ultraviolet-absorbing agent other than the silver nanoparticles and the inorganic UV-absorbing agent(s).

In some embodiments, the silver particles are present in the composition at a concentration in the range of from about 0.01% to about 10% (w/w) of the total composition. In some embodiments, the silver particles constitute at least 0.01 wt. %, at least 0.1 wt. %, at least 0.5 wt. %, at least 1 wt. %, at least 2 wt. %, at least 3 wt. %, at least 4 wt. %, at least 5 wt. % or at least 10 wt. % of the composition. In some embodiments, the silver particles constitute at most 10 wt. %, at most 5 wt. %, at most 4 wt. %, at most 3 wt. %, at most 2 wt. %, at most 1 wt. %, at most 0.5 wt. %, or at most 0.1 wt. % of the composition.

In some embodiments, the composition is in a form selected from the group consisting of an aerosol, a cream, an emulsion, a gel, a lotion, a mousse, a paste, and a liquid such as a coating or a spray.

According to a further aspect of some embodiments of the invention, there is provided a sunscreen composition as described herein, for use in protecting a subject against a harmful effect of ultraviolet radiation.

According to a further aspect of some embodiments of the invention, there is provided a sunscreen composition as described herein, for use in protecting the skin of a subject against ultraviolet radiation.

According to a further aspect of some embodiments of the invention, there is provided a sunscreen composition as described herein, for use in protecting the hair of a subject against ultraviolet radiation. In some embodiments for use in protecting the hair of a subject against ultraviolet radiation, the composition is in the form of a hair-care product selected from the group consisting of a shampoo, a conditioner and a hair mask.

In some embodiments of a use of the sunscreen composition, the subject is a human subject. In other embodiments, the sunscreen composition is used for protecting non-human animal subjects against ultraviolet radiation.

In some embodiments, protecting against ultraviolet radiation comprises protecting against ultraviolet A radiation and ultraviolet B radiation.

According to a further aspect of some embodiments of the invention, there is provided a method of manufacturing a UV-protective composition, comprising combining an inorganic ultraviolet-absorbing agent as described herein with other ingredients in proportions and in a manner suitable to make a UV-protective composition as described herein. In some embodiments, the UV-protective composition is formulated as a sunscreen composition for application to human skin. In some embodiments, the composition is formulated as a composition for application to hair, such as a shampoo or conditioner. In some embodiments, the composition is formulated for application to a surface of an inanimate object, such as a lacquer, varnish or other coating. In other embodiments, the composition is formulated for impregnation of a surface of an object, for instance when the object is a fabric.

There is also provided, in accordance with an embodiment of the invention, a method of protecting a surface from UV radiation, which comprises applying to a surface in need of such protection a UV-protective composition as described herein in an amount sufficient to achieve such protection. In some embodiments, the surface is human skin. In some embodiments, the surface is non-human skin, i.e. animal skin. In some embodiments, the surface is hair. In some embodiments, the hair is human hair. In some embodiments, the hair is non-human hair, i.e. animal hair. In some embodiments, the surface is a surface of an inanimate object. In some embodiments, the surface is of a fiber or fabric.

As used herein, the term "doped zinc oxide" or "zinc oxide doped" refers to zinc oxide crystals wherein a small amount of cations (e.g., non-zinc metal cations) are incorporated within the crystal lattice, resulting in alteration of the optical properties of the zinc oxide. The name of the dopant may precede or follow such terms.

As used herein, the term "dopant" refers to cations, such as metal cations, which are introduced in low amounts into a crystalline structure.

As used herein, the term "nanoparticles" refers to particles of any suitable shape wherein the size of at least one dimension is 100 nm or less, hereinafter also referred to as the smallest dimension, and wherein a greatest size in a different dimension of the particles, also termed a greatest dimension, is of no more than about 250 nm.

For example, in some embodiments where the particles have a flake-like shape, the smallest dimension of the nanoparticles can be their thickness which can be of up to about 100 nm, while their length can be of no more than about 250 nm.

For example, in some embodiments where the particles have a rod-like shape, their cross section along their longitudinal axis could be approximated to ellipsoids having at least their minor axis constituting a smallest dimension of no more than about 100 nm and the length of the rods being no more than about 250 nm.

For example, in some embodiments where the particles have a sphere-like shape that could be approximated by three diameters one for each of the X-, Y- and Z-direction, at least one of the three diameters is not more than about 100 nm and a greatest of the three diameters can be no more than about 250 nm.

In some embodiments, the greatest dimension of the nanoparticles is not more than about 200 nm or even not more than about 150 nm.

In some embodiments, the smallest dimension of the nanoparticles is at least about 10 nm, at least about 15 nm or at least about 20 nm.

In some embodiments, the inorganic UV-absorbing agent nanoparticles are substantially invisible to the human eye, in particular when applied to a subject.

In some embodiments, the size of the particles is as determined by microscopy techniques, as known in the art.

In some embodiments, the size of the particles is as determined by Dynamic Light Scattering (DLS). In DLS, the particles are approximated to spheres of equivalent behavior and the size can be provided in term of hydrodynamic diameter. DLS also allows assessing the size distribution of a population of particles.

Distribution results can be expressed in terms of the hydrodynamic diameter for a given percentage of the cumulative particle size distribution, either in terms of numbers of particles or volumes, and are typically provided for 10%, 50% and 90% of the cumulative particle size distribution. For instance, D50 by volume refers to the maximum hydrodynamic diameter below which 50% of the sample volume exist and is alternatively termed the median diameter per volume ($D_{V50}$). D50 by number of particles refers to the maximum hydrodynamic diameter below which 50% of the number of particles exists and is alternatively termed the median diameter per number ($D_{N50}$).

In some embodiments, the nanoparticles have a cumulative particle size distribution of D50 of 100 nm or less, or a D90 of 100 nm or less, or a D95 of 100 nm or less, or a D97.5 of 100 nm or less or a D99 of 100 nm or less, i.e. 50%, 90%, 95%, 97.5% or 99% of the sample volume or number of UV-absorbing nanoparticles, respectively, have a hydrodynamic diameter of no greater than 100 nm.

In some embodiments, the cumulative particle size distribution of the population of nanoparticles is assessed in term of number of particles or in term of volume of the sample comprising particles having a given hydrodynamic diameter.

Any hydrodynamic diameter having a cumulative particle size distribution of at least a given percent of the population of particles, as indicated, e.g., 90% or 95% or 97.5% or 99%, whether in terms of number of particles or volume of sample, as indicated, may be referred to hereinafter as the "maximum diameter", i.e. the maximum hydrodynamic diameter of particles present in the population at the respective cumulative size distribution.

It is to be understood that the term "maximum diameter" is not intended to limit the scope of the present teachings to nanoparticles having a perfect spherical shape. This term as used herein encompasses any representative dimension of the particles at cumulative particle size distribution of at least 90%, e.g., 90% or 95% or 97.5% or 99%, or any other intermediate value, of the distribution of the population.

In general, the term "broad-spectrum UV absorption" with regard to an ultraviolet-absorbing agent refers to an ultraviolet-absorbing agent that absorbs both UVA and UVB radiation. In some embodiments, the breadth of UV absorption may be measured according to the Critical Wavelength Method, wherein an ultraviolet-absorbing agent is considered to provide broad spectrum absorption when the critical wavelength is greater than 370 nm, and unless otherwise noted, in the present disclosure the term "broad-spectrum UV absorption" as used herein is determined on the basis of the critical wavelength.

As used herein, the term "critical wavelength" is defined as the wavelength at which the area under the absorbance spectrum from 290 nm to the critical wavelength constitutes 90% of the integral of the absorbance spectrum in the range from 290 nm to 400 nm.

In some instances, noted as such herein, the term "broad-spectrum UV absorption" with regard to an ultraviolet-absorbing agent refers to the situation in which the area under the curve (AUC) formed by the UV-absorption of the agent as a function of wavelength in the range of 280 nm to 400 nm ($AUC_{280-400}$) is at least 75% of the AUC formed by the same agent at the same concentration in the range of 280 nm to 700 nm ($AUC_{280-700}$). Similarly, where noted as such herein, the terms "broader-spectrum UV absorption" and "broadest spectrum UV absorption" with respect to a UV-absorbing agent refer respectively to the situation in which the area under the curve (AUC) formed by the absorption of the agent as a function of wavelength in the range of 280 nm to 400 nm ($AUC_{280-400}$) is at least 85% or 95% of the AUC formed by the same agent at the same concentration in the range of 280 nm to 700 nm ($AUC_{280-700}$).

As used herein, the term "ultraviolet-absorbing agent" refers to an agent which, when present in a composition at up to 50% (w/w) of the total composition, provides at least 50% absorption of ultraviolet light in the wavelength range of from 290 nm to 400 nm.

As used herein, the terms "generally devoid of an organic ultraviolet-absorbing agent", "considerably devoid of an organic ultraviolet-absorbing agent", "significantly devoid of an organic ultraviolet-absorbing agent", "substantially devoid of an organic ultraviolet-absorbing agent", "essentially devoid of an organic ultraviolet-absorbing agent", "substantively devoid of an organic ultraviolet-absorbing agent" and "devoid of an organic ultraviolet-absorbing agent" refer respectively to a composition in which UV-absorbing organic material, if included, present in the composition at a concentration which provides absorption of not more than 50%, not more than 40%, not more than 30%, not more than 20%, not more than 10%, not more than 1% or not more than 0.5% of ultraviolet light in the wavelength range of from 290 nm to 400 nm.

As used herein, the terms "generally devoid of an additional ultraviolet-absorbing agent", "considerably devoid of an additional ultraviolet-absorbing agent", "significantly devoid of an additional ultraviolet-absorbing agent", "substantially devoid of an additional ultraviolet-absorbing agent", "essentially devoid of an additional ultraviolet-absorbing agent", "substantively devoid of an additional ultraviolet-absorbing agent" and "devoid of an additional ultraviolet-absorbing agent" refer respectively to a composition which is UV-absorbing material other than that specifically disclosed as being present in the composition, if included in the composition, is present at a concentration which provides absorption of not more than 50%, not more than 40%, not more than 30%, not more than 20%, not more than 10%, not more than 1% or not more than 0.5% of ultraviolet light in the wavelength range of from 290 nm to 400 nm.

Aspects and embodiments of the invention are described in the specification herein below and in the appended claims.

Unless otherwise defined, all technical and scientific terms used herein have the same meaning as commonly understood by one of ordinary skill in the art to which the invention pertains. In case of conflict, the specification, including definitions, will take precedence.

As used herein, the terms "comprising", "including", "having" and grammatical variants thereof are to be taken as specifying the stated features, integers, steps or components, but do not preclude the addition of one or more additional features, integers, steps, components or groups thereof. Thus the terms "comprising", "including", "having" and grammatical variants thereof encompass the terms "consisting of" and "consisting essentially of", but are not limited to such cases.

As used herein, the indefinite articles "a" and "an" mean "at least one" or "one or more" unless the context clearly dictates otherwise.

In the discussion, unless otherwise stated, adjectives such as "substantially" and "about" that modify a condition or relationship characteristic of a feature or features of an embodiment of the present technology, are to be understood to mean that the condition or characteristic is defined within tolerances that are acceptable for operation of the embodiment for an application for which it is intended. In particular, when a numerical value is preceded by the term "about", the term "about" is intended to indicate +/−10% of the mentioned value.

Additional aspects of embodiments of the invention will be set forth in the detailed description which follows, and in part will be readily apparent to those skilled in the art from the description or recognized by practicing embodiments of the invention as described in the written description and claims hereof, as well as the appended drawings. Various features and sub-combinations of embodiments of the invention may be employed without reference to other features and sub-combinations.

It is to be understood that both the foregoing general description and the following detailed description, including the materials, methods and examples, are merely exemplary, and are intended to provide an overview or framework to understanding the nature and character of the invention as it is claimed, and are not intended to be necessarily limiting.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1C is a correlation to a UV absorbance spectrum of bismuth vanadate powder as compared to absorbance by zinc oxide powder, as determined by the integrated sphere method;

FIG. 1D-A is a correlation to a UV absorbance spectrum of zinc oxide powder doped with either 5% manganese or 5% copper on a molar basis, as determined by the integrated sphere method, undoped zinc oxide reference being included for comparative purposes;

FIG. 1D-B is a correlation to a UV absorbance spectrum of zinc oxide powder doped with different molar percentage concentrations of copper, as determined by the integrated sphere method, undoped zinc oxide reference being included for comparative purposes;

FIG. 3A-A is a High resolution Scanning Electron Microscopy (HRSEM) image of barium titanate nanoparticles used in implementing a specific embodiment of the invention described herein;

FIG. 3A-B is a HRSEM image of a titanium dioxide reference for comparative purposes;

FIGS. 3B-A and 3B-B are different magnifications of High resolution Scanning Electron Microscopy (HRSEM) images of bismuth oxide nanoparticles used in implementing a specific embodiment of the invention described herein;

FIGS. 3D-A, 3D-B, 3D-C and 3D-D are different magnifications of High resolution Scanning Electron Microscopy (HRSEM) images of copper-doped zinc oxide nanoparticles used in implementing a specific embodiment of the invention described herein;

FIG. 4D-A shows UV absorbance spectra of different concentrations of manganese-doped zinc oxide, undoped zinc oxide reference being included for comparative purposes;

FIG. 4D-B shows UV absorbance spectra of different concentrations of copper-doped zinc oxide, undoped zinc oxide reference at each concentration being included for comparative purposes;

FIG. 4D-C is a close-up view over a sub-range of what is shown in FIG. 4D-B;

DETAILED DESCRIPTION OF SOME EMBODIMENTS

Figure 1A:
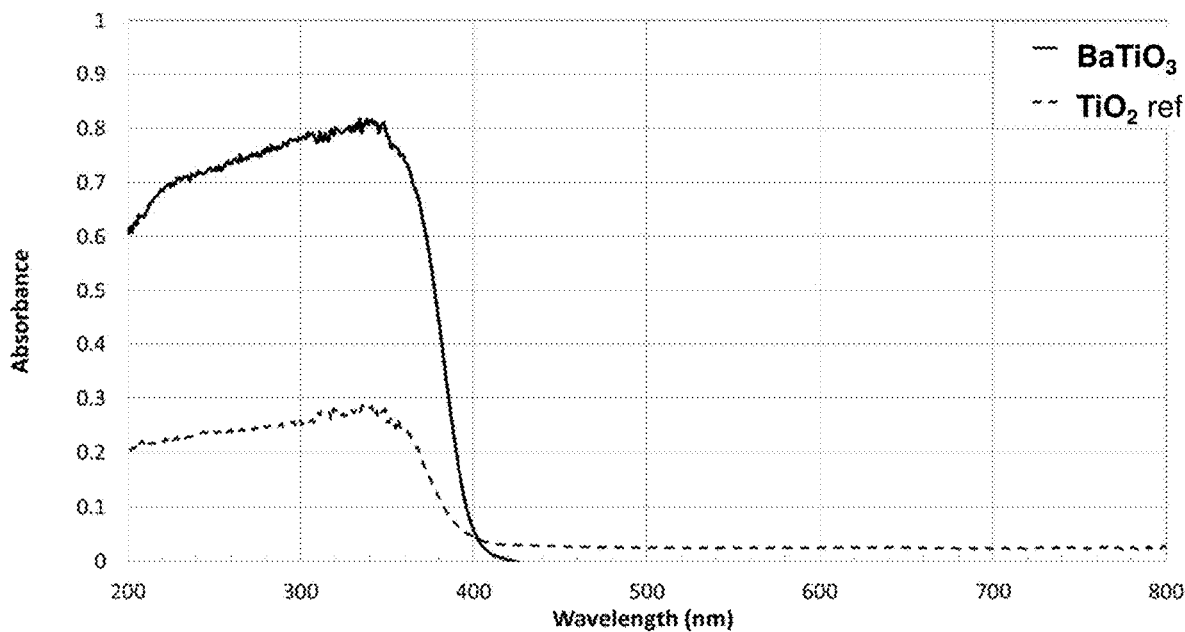
FIG. 1A is a correlation to a UV absorbance spectrum of barium titanate powder as compared to absorbance by titanium dioxide powder, as determined by the integrated sphere method.

As noted, above, there is provided, in accordance with an embodiment of the invention, a UV-protective composition which comprises particles of at least one inorganic UV-absorbing agent selected from the group consisting of (i) barium titanate ($BaTiO_3$), (ii) bismuth oxide ($Bi_2O_3$), (iii) bismuth vanadate ($BiVO_4$), and (iv) doped zinc oxide (ZnO).

It is known that in addition to absorbing ultraviolet radiation, UV-absorbing agents, including the inorganic UV-absorbing agents mentioned above, when present as large particles (e.g., dimensions in each of the X-, Y- and Z-directions being greater than 100 nanometers (nm), resulting for instance in a hydrodynamic diameter of more than 100 nm as measured by DLS) may also effectively absorb radiation having wavelengths of greater than about 400 nm. Accordingly, compositions comprising such large particles of such UV-absorbing agents may provide protection against ultraviolet radiation having wavelengths up to at least 400 nm. However, in the case in which the UV-protective composition is a sunscreen composition which comprises at least one of the aforementioned inorganic UV-absorbing agents, but which sunscreen composition also contains particles that absorb light at wavelengths in the range of 400-800 nm, the behavior of the sunscreen composition is similar to some commercially-available sunscreen compositions comprising organic UV radiation absorbing agents and/or complex combinations of UV-protective agents, i.e.

the sunscreen will be visible on the end-user because of the absorption in the visible range.

It has surprisingly been found by the present Inventors that, although reduction of particle size of known inorganic UV-absorbing agents to nanometric dimensions (e.g., below 1 micrometer (μm), typically below 100 nm) is known to significantly reduce the maximum wavelength of light, including UV light, which is effectively absorbed by the particles, compositions as described herein, such as sunscreen compositions, which contain one or more of the aforesaid inorganic UV-absorbing agents, milled to nanoparticle size, still provide substantial absorption of UV radiation of wavelength from 280 nm (or shorter wavelengths) up to about 400 nm, thus providing broad-spectrum protection against both UVA and UVB radiation, even in the absence of additional ultraviolet-absorbing agents.

Thus, in some embodiments, compositions disclosed herein, such as sunscreen compositions, comprise particles of one or more of said inorganic UV-absorbing agents, wherein at least 50% of the particles are nanoparticles, in terms of at least one of number of particles and volume of particles. In some embodiments, at least 90% or at least 95% or at least 97.5% or even at least 99% of the particles, in terms of at least one of number of particles and volume of particles, are nanoparticles.

In some embodiments, the at least one dimension of the inorganic UV-absorbing nanoparticles is expressed in terms of the hydrodynamic diameter as measured by DLS.

In some embodiments, the cumulative particle size distribution in a sample is assessed in terms of the number of particles in the sample (denoted $D_N$). In some embodiments, the cumulative particle size distribution in a sample is assessed in terms of the volume of particles in the sample (denoted $D_V$).

In some embodiments, the maximum diameter of the nanoparticles is assessed for population distribution measured in terms of number of particles and percentage thereof. In some embodiments, the maximum diameter of the nanoparticles is assessed for population distribution measured in terms of sample volume of particles and percentage thereof.

In some embodiments, the inorganic UV-absorbing agent nanoparticles in the composition are substantially invisible to the human eye, in particular when applied to the skin or hair of a subject or when applied to an inanimate surface, due to their small size.

In some embodiments, the inorganic UV-absorbing agent nanoparticles are blended into a colored composition and need not be substantially transparent and/or invisible, for instance when used in a make-up product, such as a foundation, which is slightly tinted when applied to the skin of a subject, or when used in a stain or paint.

According to an aspect of some embodiments of the invention, there is provided a sunscreen composition comprising a UV-absorbing agent selected from the group consisting of (i) barium titanate ($BaTiO_3$), (ii) bismuth oxide ($Bi_2O_3$), (iii) bismuth vanadate ($BiVO_4$), and (iv) doped zinc oxide (ZnO), as well as mixtures thereof.

According to a further aspect of some embodiments of the invention, there is provided a sunscreen composition comprising at least one of the aforementioned inorganic UV-absorbing agents, for use in protecting the skin of a subject, such as a human subject, against ultraviolet radiation, in some embodiments providing broad-spectrum protection against both ultraviolet A and ultraviolet B radiation.

According to a further aspect of some embodiments of the invention, there is provided a sunscreen composition comprising at least one of the aforementioned inorganic UV-absorbing agents, for use in protecting the hair of a subject, such as a human subject, against ultraviolet radiation, in some embodiments against both ultraviolet A and ultraviolet B radiation.

According to a further aspect of some embodiments of the invention, there is provided a method of protecting the skin of a subject against ultraviolet radiation, the method comprising applying to the skin of the subject a sunscreen composition comprising at least one of the aforementioned inorganic UV-absorbing agents. In some embodiments, the sunscreen composition is in a form selected from the group consisting of an aerosol, a cream, an emulsion, a gel, a lotion, a mousse, a paste and a spray. There is also provided a method of protecting the hair of a subject against ultraviolet radiation, the method comprising applying to the hair of the subject a hair-protective composition comprising at least one of the aforementioned inorganic UV-absorbing agents. In some embodiments, the hair protective composition is in a form of a shampoo or conditioner. There is also provided a method of protecting the surface of an inanimate object against ultraviolet radiation, the method comprising applying to the surface of the inanimate object a UV-protective composition comprising at least one of the aforementioned inorganic UV-absorbing agents. For methods of protecting the surface of inanimate objects, in addition to being in one of the forms mentioned above, the UV-protective composition may be in the form of a liquid, and applied, for example, as coating. Methods of applying UV-protective compositions to objects or sunscreen compositions to subjects or surfaces are known and need not be detailed herein.

According to a further aspect of some embodiments of the invention, there is provided the use of at least one of the aforementioned inorganic UV-absorbing agents, in the manufacture of a composition for protection of the skin of a subject against ultraviolet radiation.

According to a further aspect of some embodiments of the invention, there is provided the use of at least one of the aforementioned inorganic UV-absorbing agents in the manufacture of a composition for protection of the hair of a subject against ultraviolet radiation.

Additionally, the aforementioned inorganic UV-absorbing agents can be used in the manufacture of a composition for protection of the surface of an object against ultraviolet radiation.

According to a further aspect of some embodiments of the invention, there is provided a method of manufacturing UV-protective composition, comprising combining an inorganic UV-absorbing agent as described herein with other ingredients in proportions and in a manner suitable to make a UV-protective composition as described herein. In some embodiments, the UV-protective composition is formulated as a sunscreen composition for application to human skin. In some embodiments, the composition is formulated as a composition for application to hair, such as a shampoo or conditioner. In some embodiments, the composition is formulated for application to an inanimate surface, such as a varnish. Methods for formulating such compositions, e.g. sunscreens, shampoos, conditioners, and varnishes, are well-known in the art.

In some embodiments of the compositions, use or methods disclosed herein, the inorganic UV-absorbing agent or combination thereof is present in the composition at a concentration of from about 0.001% (w/w) to about 40% (w/w), from about 0.01% (w/w) to about 30% (w/w), from about 0.1% (w/w) to about 20% (w/w) or even from about 0.1% (w/w) to about 15% (w/w) of the final composition. In some embodiments, the inorganic UV-absorbing agent constitutes at least 0.01 wt. %, at least 0.1 wt. %, at least 0.5 wt. %, at least 1 wt. %, at least 2 wt. %, at least 3 wt. %, at least 4 wt. %, at least 5 wt. %, at least 10 wt. %, at least 15 wt. %, at least 20 wt. %, at least 25 wt. %, at least 30 wt. %, at least 35 wt. %, or at least 40 wt. %. of the composition. In some embodiments, the inorganic UV-absorbing agent constitutes at most 40 wt. %, at most 35 wt. %, at most 30 wt. %, at most 25 wt. %, at most 20 wt. %, at most 15 wt. %, at most 10 wt. %, at most 5 wt. %, at most 4 wt. %, at most 3 wt. %, at most 2 wt. %, at most 1 wt. %, at most 0.5 wt. %, at most 0.1 wt. % or at most 0.01 wt. % of the composition.

In some embodiments of the composition, use or method disclosed herein, the inorganic UV-absorbing agent or combination thereof is present in the composition as nanoparticles having at least one dimension of up to about 100 nm. In some embodiments, the nanoparticles have at least one dimension in the range of from about 10 nm to about 80 nm, from about 10 to about 70 nm, from about 20 to about 70 nm or from about 20 to about 60 nm. In some particular embodiments, the nanoparticles have at least one dimension of about 30 nm.

In some embodiments, the aforementioned dimensions or ranges of dimensions apply to at least 50%, at least 90%, at least 95%, at least 97.5% or at least 99% of the population of the nanoparticles on a volume basis. In some embodiments, the aforementioned dimensions or ranges of dimensions apply to at least 50%, at least 90%, at least 95%, or at least 97.5% or at least 99% of the population of the nanoparticles on a number basis.

In some embodiments, the aforesaid smallest dimension of the inorganic UV-absorbing agent nanoparticles, is estimated based on the hydrodynamic diameter of the particles as measured by DLS. In some embodiments, the population distribution of the particles is expressed in terms of the cumulative particle size distribution, according to the number of particles in a sample. In some embodiments, the population distribution of the particles is expressed in terms of the cumulative particle size distribution of a sample volume of particles.

In some embodiments of the composition, use or method disclosed herein, the composition contains less than 5 wt. % organic UV-absorbing agents. In some embodiments the composition contains less than 4 wt. %, 3 wt. %, 2 wt. % or 1 wt. % organic UV-absorbing agents. In some embodiments the composition is largely free of organic ultraviolet-absorbing agents, i.e. the composition contains less than 0.5 wt. % organic UV-absorbing agents. In some embodiments the composition is mostly free of organic UV-absorbing agents, i.e. the composition contains less than 0.1 wt. % organic UV-absorbing agents. In some embodiments the composition is principally free of organic ultraviolet-absorbing agents, i.e. the composition contains less than 0.05 wt. % organic UV-absorbing agents. In some embodiments the composition is fundamentally free of organic UV-absorbing agents, i.e. the composition contains less than 0.01 wt. % organic UV absorbing agents. In some embodiments of the composition, use or method disclosed herein, the composition is generally devoid of organic ultraviolet-absorbing agents, considerably devoid of organic ultraviolet-absorbing agents, significantly devoid of organic ultraviolet-absorbing agents, substantially devoid of organic ultraviolet-absorbing agents, essentially devoid of organic ultraviolet-absorbing agents, substantively devoid of organic ultraviolet-absorbing agents or devoid of organic ultraviolet-absorbing agents.

In some embodiments of the composition, use or method disclosed herein, the composition contains less than 10 wt. % additional UV-absorbing agents. In some embodiments the composition contains less than 5 wt. %, less than 4 wt. %, less than 3 wt. %, less than 2 wt. % or less than 1 wt. % additional UV-absorbing agents. In some embodiments the composition is largely free of additional ultraviolet-absorbing agents, i.e. the composition contains less than 0.5 wt. % additional UV-absorbing agents. In some embodiments the composition is mostly free of additional UV-absorbing agents, i.e. the composition contains less than 0.1 wt. % additional UV-absorbing agents. In some embodiments the composition is principally free of additional ultraviolet-absorbing agents, i.e. the composition contains less than 0.05 wt. % additional UV-absorbing agents. In some embodiments the composition is fundamentally free of additional UV-absorbing agents, i.e. the composition contains less than 0.01 wt. % additional UV absorbing agents. In some embodiments of the composition, use or method disclosed herein, the composition is generally devoid of additional ultraviolet-absorbing agents, considerably devoid of additional ultraviolet-absorbing agents, significantly devoid of additional ultraviolet-absorbing agents, substantially devoid of additional ultraviolet-absorbing agents, essentially additional of organic ultraviolet-absorbing agents, substantively additional of organic ultraviolet-absorbing agents or devoid of additional ultraviolet-absorbing agents.

In some embodiments of the composition, use or method disclosed herein, the inorganic UV-absorbing agent or mixture of such agents is the sole ultraviolet-absorbing agent in the composition.

In some embodiments of the composition, use or method disclosed herein, the composition further comprises silver metal particles.

In some embodiments, the silver metal particles are present in the composition as nanoparticles. In some embodiments, the silver nanoparticles have at least one dimension of up to about 50 nm. In some embodiments, the silver nanoparticles have at least one dimension of up to about 40 nm. In some embodiments, the silver nanoparticles have at least one dimension of up to about 30 nm. In some embodiments, the silver nanoparticles have at least one dimension in the range of from about 10 nm to up to about 50 nm.

In some embodiments, the aforementioned dimensions or ranges of dimensions apply to at least 50%, at least 90%, at least 95%, at least 97.5% or at least 99% of the population of the silver nanoparticles on a volume basis. In some embodiments, the aforementioned dimensions or ranges of dimensions apply to at least 50%, at least 90%, at least 95%, at least 97.5% or at least 99% of the population of the silver nanoparticles on a number basis.

In some embodiments, the aforesaid at least one dimension of the silver nanoparticles is estimated based on the hydrodynamic diameter of the particles as measured by DLS. In some embodiments, the population distribution of the particles is expressed in terms of the cumulative particle size distribution according to the number of particles in a sample. In some embodiments, the population distribution of the particles is expressed in terms of the cumulative particle size distribution of a sample volume of particles.

In some embodiments, the silver nanoparticles are present in the composition at a concentration in the range of from about 0.01% to about 10% (w/w) of the total composition. In some embodiments, the silver nanoparticles are present in the composition at a concentration in the range of from about 0.01% to about 5% (w/w), from about 0.05% to about 5% (w/w), or from about 0.1% to about 2% (w/w) of the total composition. In some preferred embodiments, the silver nanoparticles are present in the composition at a concentration of about 1% (w/w) or about 2% (w/w) of the total composition. In some embodiments, the silver particles constitute at least 0.01 wt. %, at least 0.1 wt. %, at least 0.5 wt. %, at least 1 wt. %, at least 2 wt. %, at least 3 wt. %, at least 4 wt. %, at least 5 wt. % or at least 10 wt. % of the composition. In some embodiments, the silver particles constitute at most 10 wt. %, at most 5 wt. %, at most 4 wt. %, at most 3 wt. %, at most 2 wt. %, at most 1 wt. %, at most 0.5 wt. %, or at most 0.1 wt. % of the composition.

In some embodiments of the composition, use or method disclosed herein, the composition is a composition for human or animal use, formulated as a topical composition. The topical composition may optionally be provided in a form selected from the group consisting of a cream, an emulsion, a gel, a lotion, a mousse, a paste and a spray. If desired, the composition can also be formulated into make-up cosmetics, for example, foundation, blusher, etc.

In some embodiments, the topical composition further comprises a dermatologically or cosmetically or pharmaceutically acceptable carrier.

In some embodiments, the topical composition further comprises one or more dermatologically or cosmetically or pharmaceutically acceptable additives or excipients, such as colorants, preservatives, fragrances, humectants, emollients, emulsifiers, waterproofing agents, surfactants, dispersants, thickeners, viscosity modifiers, anti-foaming agents, conditioning agents, antioxidants and the like. Such additives or excipients and the concentrations at which each can effectively accomplish its respective functions, are known to persons skilled in the pertinent art and need not be further detailed.

In some embodiments, the topical composition is a sunscreen composition.

In some embodiments, the subject is a human subject.

The skin to which the composition is formulated to be applied, or to which the composition is applied, may be the skin of the face, of the arms, of the legs, of the neck of the torso, or of any other area of the body that can be exposed to UV radiation.

In some embodiments, a sunscreen composition as disclosed herein is applied to the skin of the subject prior to or during exposure to UV radiation. In some embodiments, the composition is reapplied intermittently, for example every 10 hours, every 9 hours, every 8 hours, every 7 hours, every 6 hours, every 5 hours, every 4 hours, every 3 hours, every 2 hours or every hour during exposure to UV radiation.

In some embodiments, the composition is for protecting the hair of a subject against ultraviolet radiation and is provided in a form selected from the group consisting of a cream, an emulsion, a gel, a lotion, a mousse, a paste and a spray. In some embodiments, the composition is provided in the form of a shampoo, a conditioner or a hair mask.

In some embodiments, the composition is formulated to be applied to the hair, or is applied to the hair, for a fixed period of time, such as up to 1 minute, up to 2 minutes, up to 3 minutes, up to 4 minutes, up to 5 minutes, up to 10 minutes, up to 15 minutes, up to 20 minutes, up to 25 minutes or even up to 30 minutes prior to rinsing. In some embodiments, the conditioner or hair mask is formulated for application to the hair, or is applied to the hair, without rinsing, such that the conditioner or hair mask remains on the hair.

In some embodiments of the composition, use or method disclosed herein, the composition is a composition for the protection of inanimate objects against UV radiation, formulated in any form suitable for the surface of surfaces to which the composition is to be applied. The composition can be suitable for porous or non-porous surfaces, and for instance, in the form of an aerosol, a cream, an emulsion, a gel, a liquid coat, a mousse, a paste and a spray. It can be applied during the manufacturing of the object and/or periodically thereafter.

EXAMPLES

Materials and Methods
Materials:
All materials, unless otherwise indicated, were purchased from Sigma Aldrich as follows:
Barium titanate at purity of 99% (CAS 12047-27-7)
Bismuth oxide at purity of 99% (CAS 1304-76-3)
Bismuth vanadate at purity of 99% (CAS 14059-33-7, Alfa Aesar)
Zinc oxide at purity of 99.9% (CAS 1314-13-2)
Titanium dioxide at purity of 99.9% (CAS 13463-67-7)
Copper oxide at purity of 99.0% (CAS 1317-38-0)
Manganese oxide at purity of 99.0% (CAS 1313-13-9)
Poly Acrylic Acid Sodium base (PAA) (CAS 9003-04-7)
Silver particles 10 nm (Sigma Aldrich Cat. No.—730785)

Example 1: Absorbance of UV Radiation by Powders of Barium Titanate, Bismuth Oxide, Bismuth Vanadate, and 5% Doped Zinc Oxide Absorbance correlation of dry powders of barium titanate, bismuth oxide, bismuth vanadate, and 5% doped zinc oxide powder over the wavelength range of 200-800 nm was calculated using a Cary 300 UV-Vis spectrophotometer with an integrated sphere detector (Agilent Technologies, Santa Clara, Calif., USA), with dry titanium dioxide powder as reference.

Preparation of Doped Zinc Oxide Powder
In order to obtain 5% doped zinc oxide in molar percentage of doping agent, 500 g of zinc oxide powder (MW=81.4084 g/mol) having an average particle size of less than about 5 μm was mixed with either 24.43 g copper oxide powder (CuO, MW=79.5454 g/mol) or 26.70 g manganese oxide powder ($MnO_2$, MW=86.9368 g/mol) as source for copper or manganese dopant. Mixing was carried out in a Pulverisette 2 mortar grinder (Fritsch, GmbH) for about 10 minutes at 70 rpm to obtain a homogenous powder.

The homogenous powder was transferred to a 500 ml alumina crucible and then heated in a ceramic oven (Vulcan 3-1750) at a heating rate of 40° C./min until a temperature of 1000° C. was reached. The powder was subsequently heated at this elevated temperature for 24 hours. It has been reported (Florian Norindr, Ph.D. thesis, University of Southampton Research Repository, September 2009) that at this temperature, sufficient energy is provided for the dopant ions to diffuse into the ZnO host matrix and dope it.

After heating for 24 hours, the powder was allowed to cool to room temperature (circa 23° C.) and then ground again for 10 minutes at 70 rpm by the Pulverisette 2 mortar grinder.

Absorbance Measurements
Briefly, the absorbance of the samples was qualitatively estimated by subtracting the amount of light reflected from the powder sample, gathered by the integrated sphere detector of the spectrophotometer, from the amount of light reflected from a white surface (which reflects all incident light). Since the extent of penetration of the light into the samples and the extent of scattering of the sample is unknown, this measurement provides an absorbance profile of the sample rather than a true quantitative measurement.

Results, showing correlation to absorbance as a function of wavelength, determined by diffuse reflection measurement gathered by the integrated sphere method, are presented in FIGS. 1A, 1B, 1C and 1D.

As seen in FIG. 1A, titanium dioxide has a relatively constant UV absorbance from 200 nm to about 350 nm, with very low absorbance above 400 nm. Barium titanate has significantly higher UV absorbance from 200 nm to about 350 nm, at least comparable to that of zinc oxide (not shown), with negligible absorbance above about 410 nm.

Figure 1B:
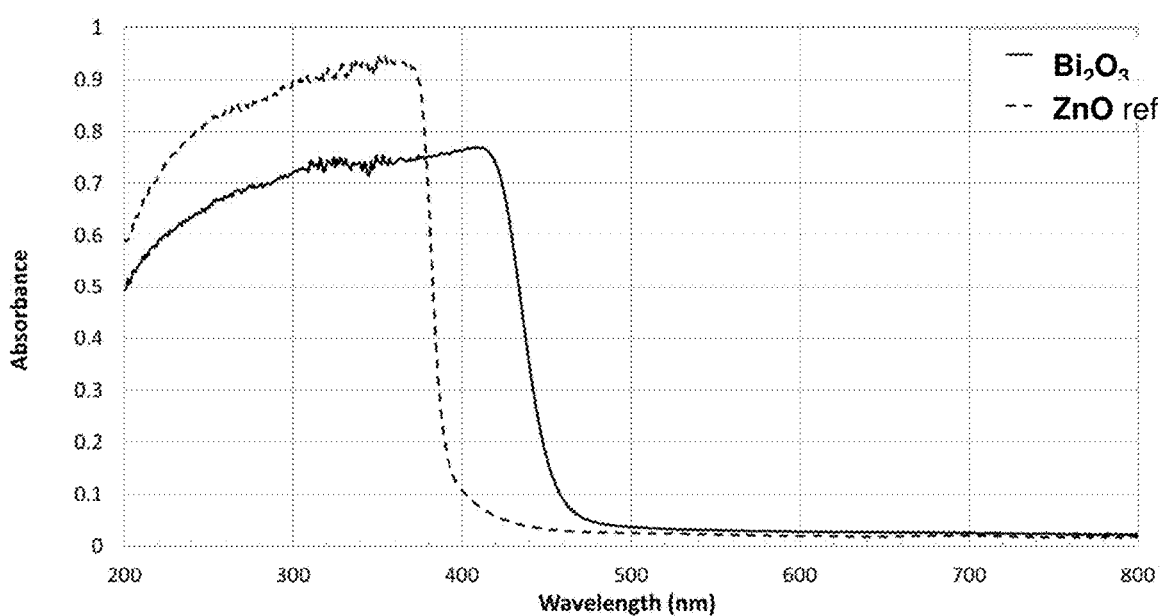
FIG. 1B is a correlation to a UV absorbance spectrum of bismuth oxide powder as compared to absorbance by zinc oxide powder, as determined by the integrated sphere method.

As seen in FIG. 1B, undoped zinc oxide has high UV absorbance from 200 nm to about 375 nm, with negligible absorbance above 390 nm. Bismuth oxide has high UV absorbance from 200 nm to about 440 nm, with negligible absorbance above 460 nm.

As seen in FIG. 1C, undoped zinc oxide has high UV absorbance from 200 nm to about 375 nm, with negligible absorbance above 390 nm. Bismuth vanadate has high UV absorbance from 200 nm to at least about 470 nm.

As seen in FIG. 1D-A, absorbance in the 380-400 nm wavelength range was significantly greater for zinc oxide powder doped with either copper or manganese as compared to the absorbance of the undoped zinc oxide reference powder. At 400 nm, absorbance of zinc oxide powder doped with copper was greater than that of zinc oxide powder doped with manganese. Doping of the zinc oxide was confirmed by XRD measurement, which showed that the crystal dimensions of the zinc oxide were altered by doping with 5% copper molar percentage, as compared to the undoped zinc oxide reference powder.

FIG. 1D-B shows the absorbance of UV radiation over the wavelength range of 200-800 nm for zinc oxide doped with various molar percentage concentrations of dopant to matrix, namely with 1%, 3% and 5% copper. As seen in this figure, zinc oxide powder doped with copper at each of the tested concentrations showed significantly greater absorbance of UV radiation in the 380-400 nm wavelength range as compared to the absorbance of undoped zinc oxide reference powder in the same wavelength range. In the present experiment, doping the zinc oxide matrix with 3% or 5% of copper oxide (molar percentage) yielded similar results.

Example 2: Preparation of Nanoparticles

Doped zinc oxide was prepared as described in Example 1. Nanoparticles of barium titanate, bismuth oxide, bismuth vanadate and doped zinc oxide were prepared from the corresponding powder having particle size of greater than about 5 μm by milling in an Attritor grinding mill (HD-01 by Union Process®, Akron, Ohio, USA) using a batch size of 200 g with solid loading 10% (20 g) as follows.

All materials were weighed using an analytical scale (Mettler Toledo, Columbus, Ohio, USA). 20 g of solid PAA dispersant was weighed and dissolved in 180 g deionized water as solvent to provide a 10% (w/w) PAA solution. 20 g of the relevant powder was weighed and introduced into the PAA solution to provide a PAA dispersant:inorganic UV-absorbing agent ratio of 1:1 yielding a slurry of inorganic UV-absorbing agent.

In each case, the slurry was placed in a zirconia pot with 2300 g of 2 mm diameter zirconia grinding beads. The pot was placed in the grinding mill, and the grinding mill activated at 700 RPM for 100 hours at 25° C. The resulting product was a 9% (w/w) suspension of inorganic UV-absorbing agent nanoparticles in water, the inorganic solid content being assessed by oven burning as described in more detail below.

Each 9% (w/w) suspension of inorganic UV-absorbing agent nanoparticles was diluted in distilled water to obtain a concentration of 0.5%, 1.0% or 2.0% (w/w), then sonicated for 30 seconds using a Misonix Sonicator tip (Misonix, Inc.) at amplitude 100, 15 W.

The hydrodynamic diameter of the nanoparticles was determined by Dynamic Light Scattering, using a Zen 3600 Zetasizer from Malvern Instruments Ltd. (Malvern, UK) using the suspension having 0.5% inorganic UV-absorbing agent nanoparticles in water.

Figure 2A:
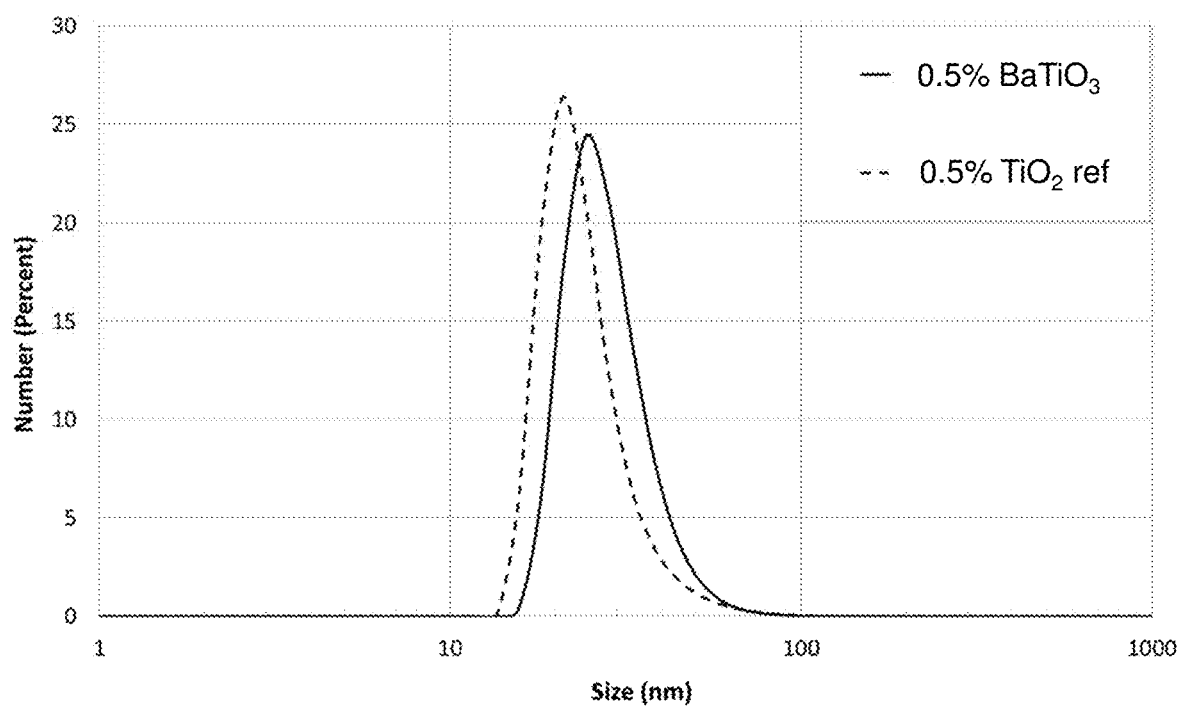
FIG. 2A is a line graph showing the distribution of barium titanate nanoparticle sizes used in implementing a specific embodiment of the invention described herein, titanium dioxide reference being included for comparative purposes.

Results, showing (a) the percentage of barium titanate and reference titanium dioxide particles having hydrodynamic diameters in the range of 1-1000 nm are presented in FIG. 2A; (b) the percentage of particles of bismuth oxide and reference undoped zinc oxide having hydrodynamic diameters in the range of 1-1000 nm are presented in FIG. 2B; (c) the percentage of bismuth vanadate and reference undoped zinc oxide particles having hydrodynamic diameters in the range of 1-1000 nm are presented in FIG. 2C; (d) the percentage of particles of undoped and doped zinc oxide having hydrodynamic diameters in the range of 1-1000 nm are presented in FIG. 2D.

As shown in FIG. 2A, the majority of barium titanate particles in suspension had hydrodynamic diameters in the size range of from about 20 nm and up to about 100 nm, mainly up to about 60 nm with a predominant peak around about 30 nm. Specifically, the cumulative particle size distribution for the hydrodynamic diameter of barium titanate particles at D95, D97.5 and D99 of the population, analyzed in terms of percentage of number of particles were found to be about 45 nm, about 50 nm and about 59 nm, respectively.

The majority of titanium dioxide particles serving as reference in suspension had hydrodynamic diameters in the size range of from about 15 nm and up to about 100 nm, mainly up to about 60 nm with a predominant peak around about 25 nm. Specifically, the cumulative particle size distribution for the hydrodynamic diameter of titanium dioxide particles at D95, D97.5 and D99 of the population, analyzed in terms of percentage of number of particles were found to be about 40 nm, about 48 nm and about 58 nm, respectively.

Figure 2B:
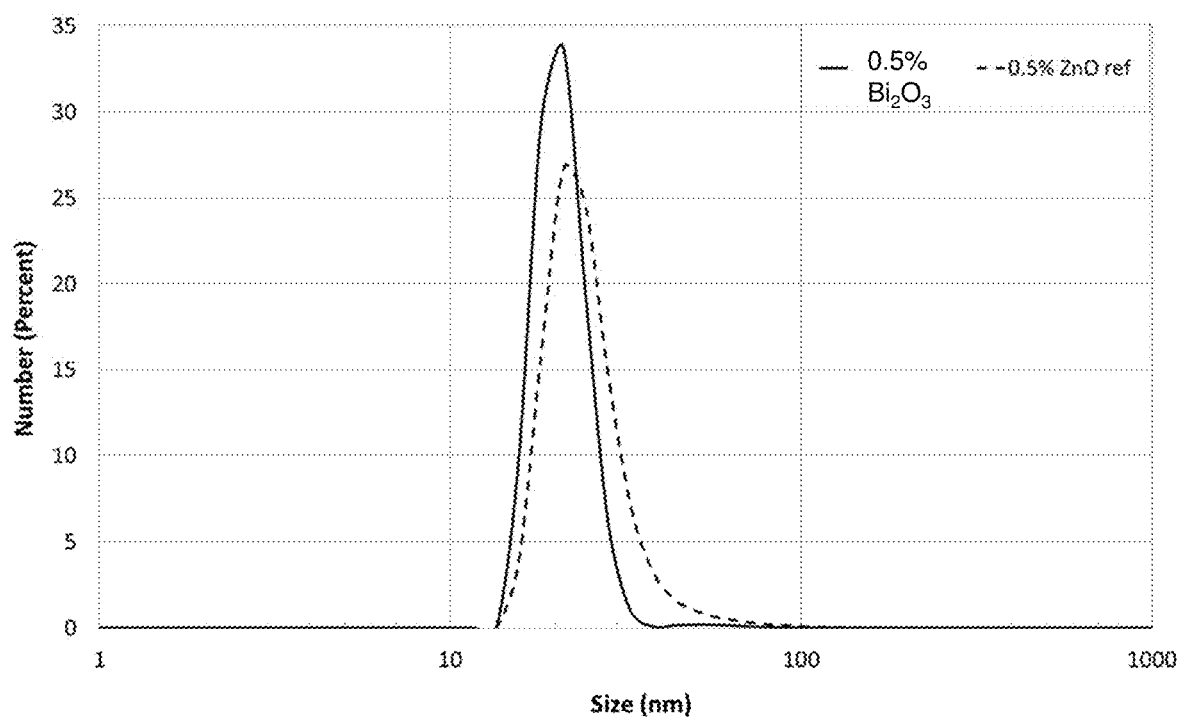
FIG. 2B is a line graph showing the distribution of bismuth oxide nanoparticle sizes used in implementing a specific embodiment of the invention described herein, zinc oxide reference being included for comparative purposes.

As shown in FIG. 2B, the majority of bismuth oxide particles in suspension had hydrodynamic diameters in the size range of from about 10 nm and up to about 100 nm, mainly up to about 50 nm with a predominant peak around about 20 nm. Specifically, the cumulative particle size distribution for the hydrodynamic diameter of the bismuth oxide nanoparticles at D95, D97.5 and D99 of the population, analyzed in terms of percentage of number of particles were found to be about 28 nm, about 31 nm and about 35 nm, respectively. For comparison, a 0.5% w/w suspension of zinc oxide serving as reference displayed maximal diameters of about 39 nm, about 48 nm and about 62 nm for same percentage of particles.

Figure 2C:
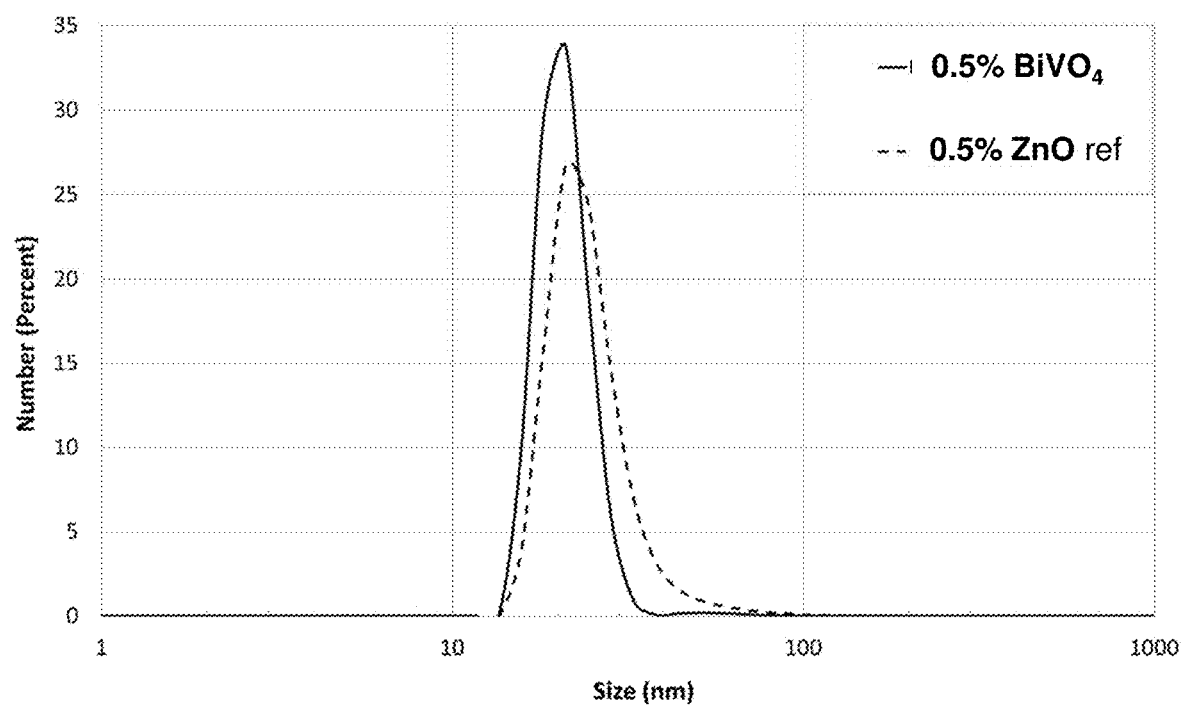
FIG. 2C is a line graph showing the distribution of bismuth vanadate nanoparticle sizes used in implementing a specific embodiment of the invention described herein, zinc oxide reference being included for comparative purposes.

As shown in FIG. 2C, the majority of bismuth vanadate particles in suspension had hydrodynamic diameters in the size range of from about 10 nm and up to about 100 nm, mainly from about 20 nm and up to about 50 nm, with a predominant peak around about 35 nm. Specifically, the cumulative particle size distribution for the hydrodynamic diameter of bismuth vanadate particles at D95, D97.5 and D99 of the population, analyzed in terms of percentage of number of particles were found to be about 36 nm, about 42 nm and about 65 nm, respectively. For comparison, a 0.5% w/w suspension of zinc oxide serving as reference displayed maximal diameters of about 39 nm, about 48 nm and about 62 nm for same percentage of particles.

Figure 2D:
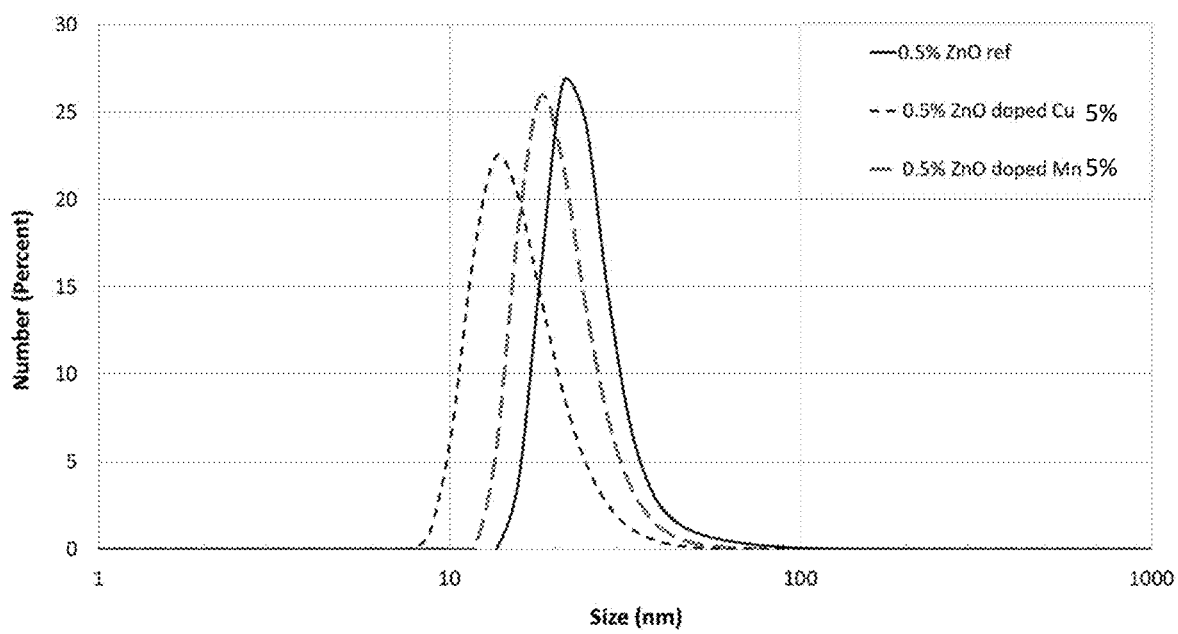
FIG. 2D is a line graph showing the distribution of copper-doped and manganese-doped zinc oxide nanoparticle sizes used in implementing a specific embodiment of the invention described herein, undoped zinc oxide reference being included for comparative purposes.

As shown in FIG. 2D, the majority of particles of undoped or manganese-doped zinc oxide in suspension had hydrodynamic diameters in the size range of from about 15 nm and up to about 100 nm, with a predominant peak around about 20 nm, while the majority of particles of copper-doped zinc oxide in suspension had hydrodynamic diameters in the size range of from about 8 nm and up to about 50 nm, with a predominant peak around about 15 nm. The cumulative particle size distribution for the hydrodynamic diameter (in nanometers) of undoped zinc oxide, copper-doped zinc oxide and manganese-doped zinc oxide at D95, D97.5 and D99 of the population, analyzed in terms of percentage of number of particles are shown in Table 1.

TABLE 1

| Material | D95 | D97.5 | D99 |
| --- | --- | --- | --- |
| undoped ZnO | 39.5 | 47.7 | 62.2 |
| 5% Cu-doped ZnO | 26.7 | 30.6 | 36.2 |
| 5% Mn-doped ZnO | 32.5 | 37.2 | 43.6 |

The nanoparticles of barium titanate, titanium dioxide, bismuth oxide, bismuth vanadate, and doped zinc oxide were also studied in dried form by High Resolution Scanning Electron Microscopy (HR-SEM) using Magellan™ 400 HSEM/TEM by Nanolab Technologies (Milpitas, Calif., USA). The images obtained are shown in FIGS. 3A-A (barium titanate), 3A-B (titanium dioxide), 3B-A and 3B-B (bismuth oxide), 3C (bismuth vanadate), and 3D-A, 3D-B, 3D-C and 3D-D (doped zinc oxide).

As shown in FIG. 3A-A, barium titanate particles having spheroid shape with diameters of less than about 100 nm, mainly less than about 60 nm, were obtained. Larger clusters are deemed non-representative, resulting from agglomeration of individual particles upon preparation of the sample for HR-SEM analysis, the drying out of the liquid carrier being known to cause such artificial outcome. The good correlation between the diameters of the particles when measured in suspension and in dried form confirms the suitability of the above-described method to prepare nanoparticles having at least one dimension (e.g., a diameter) of up to about 100 nm. FIG. 3A-B, shows particles of titanium dioxide as reference for comparative purpose.

As shown in FIG. 3A-B, titanium dioxide particles having spheroid shape with diameters of less than about 100 nm, mainly less than about 50 nm, were obtained. These results are provided as reference for comparative purposes.

As shown in FIGS. 3B-A and 3B-B, bismuth oxide particles having spheroid shape with diameters of less than about 100 nm, mainly less than about 50 nm, were obtained. Larger clusters are deemed non-representative, resulting from agglomeration of individual particles upon preparation of the sample for HR-SEM analysis, the drying out of the liquid carrier being known to cause such artificial outcome. The good correlation between the diameters of the particles when measured in suspension and in dried form confirms the suitability of the above-described method to prepare nanoparticles having at least one dimension (e.g., a diameter) of up to about 100 nm.

Figure 3C:
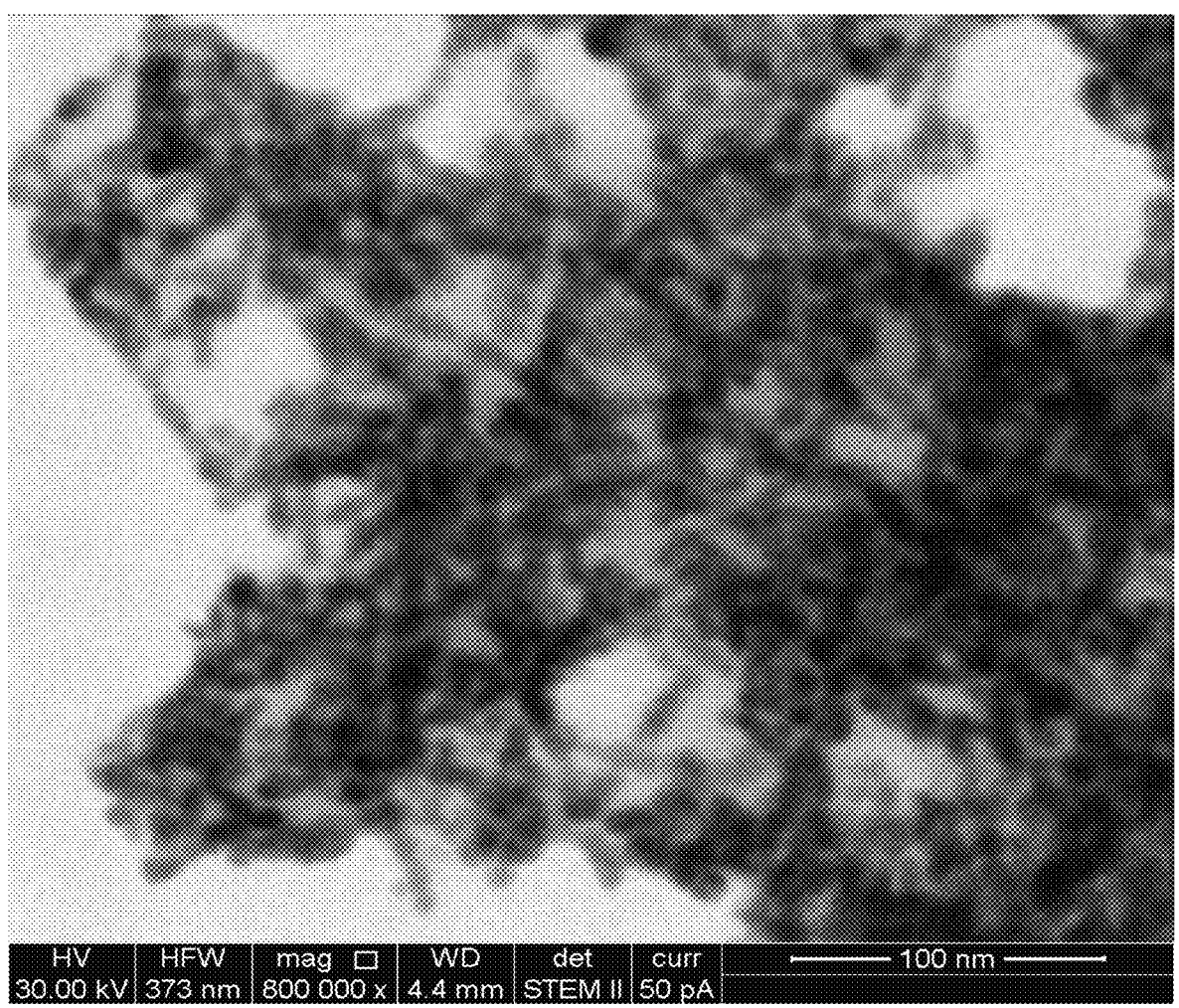
FIG. 3C is a High resolution Scanning Electron Microscopy (HRSEM) image of bismuth vanadate nanoparticles used in implementing a specific embodiment of the invention described herein.

As shown in FIG. 3C, bismuth vanadate particles having spheroid shape with diameters of less than about 100 nm, mainly about 25 nm, were obtained. Larger clusters are deemed non-representative, resulting from agglomeration of individual particles upon preparation of the sample for HR-SEM analysis, the drying out of the liquid carrier being known to cause such artificial outcome. The good correlation between the diameters of the particles when measured in suspension and in dried form confirms the suitability of the above-described method to prepare nanoparticles having at least one dimension (e.g., a diameter) of up to about 100 nm.

As shown in FIGS. 3D-A, 3D-B, 3D-C and 3D-D, each displaying a different magnification, copper doped zinc oxide particles having spheroid shape with diameters of less than about 100 nm, mainly less than about 50 nm, were obtained. Similar pictures (not shown) were obtained for manganese doped and undoped zinc oxide particles. Larger clusters are deemed non-representative, resulting from agglomeration of individual particles upon preparation of the sample for HR-SEM analysis, the drying out of the liquid carrier being known to cause such artificial outcome. The good correlation between the diameters of the particles when measured in suspension and in dried form confirms the suitability of the above-described method to prepare nanoparticles having at least one dimension (e.g., a diameter) of up to about 100 nm.

Example 3: Absorbance of UV Radiation by Inorganic UV-Absorbing Nanoparticles at Different Concentrations Barium titanate nanoparticles having a $D_N95$ of about 45 nm, a $D_N97.5$ of about 50 nm and a $D_N99$ of about 59 nm were prepared by milling to obtain a 9% (w/w) suspension, which was then diluted in water to obtain a concentration of 0.5%, 1.0% or 2.0% (w/w) and sonicated, as described in Example 2. Bismuth oxide nanoparticles of median hydrodynamic diameter (D50 of the number of particles) of about 20 nm and having a $D_N95$ of about 28 nm, a $D_N97.5$ of about 31 nm, and a $D_N99$ of about 35 nm, were prepared by milling to obtain a 9% (w/w) suspension, which was then diluted in water to obtain a concentration of 0.5%, 1.0% or 2.0% (w/w) and sonicated, as described in Example 2. Bismuth vanadate nanoparticles having a $D_N95$ of about 36 nm, a $D_N97.5$ of about 42 nm and a $D_N99$ of about 65 nm were prepared by milling to obtain a 2% (w/w) suspension, which was then diluted in water to obtain a concentration of 0.5%, 1.0% or 2.0% (w/w) and sonicated, as described in Example 2. 5% Copper-doped zinc oxide nanoparticles having a $D_N95$ of about 27 nm, a $D_N97.5$ of about 31 nm and a $D_N99$ of about 36 nm, were prepared by milling to obtain a 9% (w/w) suspension, which was then diluted in water to obtain a concentration of 0.5%, 1.0% or 2.0% (w/w) and sonicated, as described in Example 2 above. 5% Manganese-doped zinc oxide nanoparticles having a $D_N95$ of about 33 nm, a $D_N97.5$ of about 37 nm and a $D_N99$ of about 43 nm, were prepared by milling to obtain a 9% (w/w) suspension, which was then diluted in water to obtain a concentration of 0.5%, 1.0% or 2.0% (w/w) and sonicated, as described in Example 2 above.

The weight percentage of barium titanate, bismuth oxide, bismuth vanadate, copper-doped zinc oxide and manganese-doped zinc oxide following milling, as well as of the reference titanium dioxide and undoped zinc oxide, was confirmed by burning a sample of the suspension at 500° C. for 5 hours in a Vulcan 3-1750 ceramic oven. A predetermined weight (e.g., 2 gram) of the sample was placed in an aluminum crucible and the weight of the residues after evaporation of the liquid carrier and combustion of the organic components, if any, was measured using an analytical scale. Dividing the weight of the residue by the original weight of the sample provided the concentration of inorganic materials in the composition being assessed.

Absorbance of barium titanate particles over the wavelength range of 200-800 nm was measured for each concentration using a Cary 300 UV-Vis spectrophotometer with quartz cuvette (10 mm light pathway). A suspension of 2% (w/w) titanium dioxide was included as reference for comparative purposes. Results are presented in FIG. 4A.

Figure 4A:
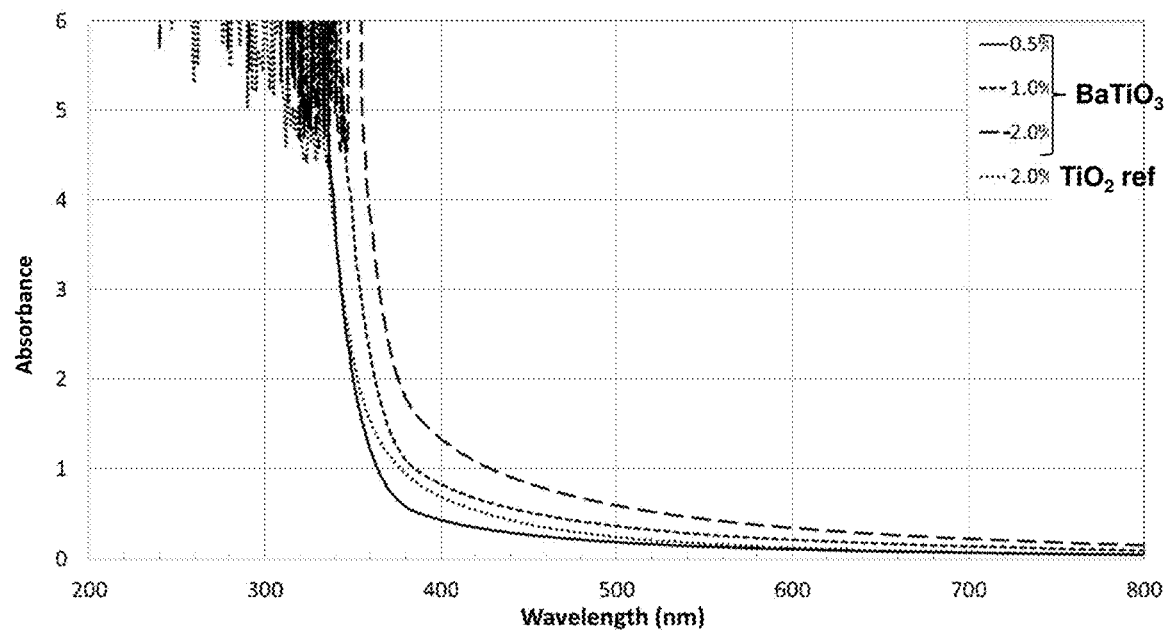
FIG. 4A shows UV absorbance spectra for three different concentrations of barium titanate nanoparticles according to the present teachings, titanium dioxide reference being included for comparative purposes.

As seen in FIG. 4A, absorption in the 360-400 nm wavelength range was greater using higher concentrations of barium titanate in the range tested. At the same concentration, barium titanate (upper long dash line) displayed a higher absorbance than reference titanium dioxide (lower dotted line), as well as a prolonged UV attenuation.

The density of $BaTiO_3$ is about 6.0 g/cm$^3$, while the density of $TiO_2$ is about 4.2 g/cm$^3$. Therefore, the number of particles in a $TiO_2$ suspension is higher than the number of particles in a $BaTiO_3$ suspension at the same concentration. Thus the physical absorption properties of barium titanate may be considered to be superior to those of titanium dioxide per same amount of particles. As the particle size distribution of the $BaTiO_3$ particles is comparable to the distribution of the particles of the $TiO_2$ reference (see FIG. 2A), such finding is believed to be significant.

Absorbance of bismuth oxide particles over the wavelength range of 200-800 nm was measured for each concentration using a Cary 300 UV-Vis spectrophotometer with quartz cuvette (10 mm light pathway). Results are presented in FIG. 4B, from which it can be seen that absorption in the 360-400 nm wavelength range was greater using higher concentrations of bismuth oxide in the range tested.

Absorbance of bismuth vanadate particles over the wavelength range of 200-800 nm was measured for each concentration using a Cary 300 UV-Vis spectrophotometer with quartz cuvette (10 mm light pathway). Results are presented in FIG. 4C, from which it can be seen that absorption in the 380-400 nm wavelength range was greater using higher concentrations of bismuth vanadate in the range tested.

It must be emphasized that the absorption curve may be shifted to the left and down by further milling to reduce the particle size, preferably coupled with maintaining or reducing the PDI, as will be further elaborated hereinbelow.

Absorbance of the 5% manganese-doped zinc oxide nanoparticles over the wavelength range of 200-800 nm was measured as described above for each concentration, and compared to that of undoped zinc oxide nanoparticles at the same concentrations. Results are presented in FIG. 4D-A, which shows that, at each of the tested concentrations, zinc oxide nanoparticles doped with 5% manganese showed significantly greater absorbance of UV radiation in the 380-400 nm wavelength range, as compared to the absorbance of undoped zinc oxide nanoparticles at the same concentrations. Absorbance in the 380-400 nm range was found to increase with zinc oxide concentration for the tested concentrations.

Figure 4B:
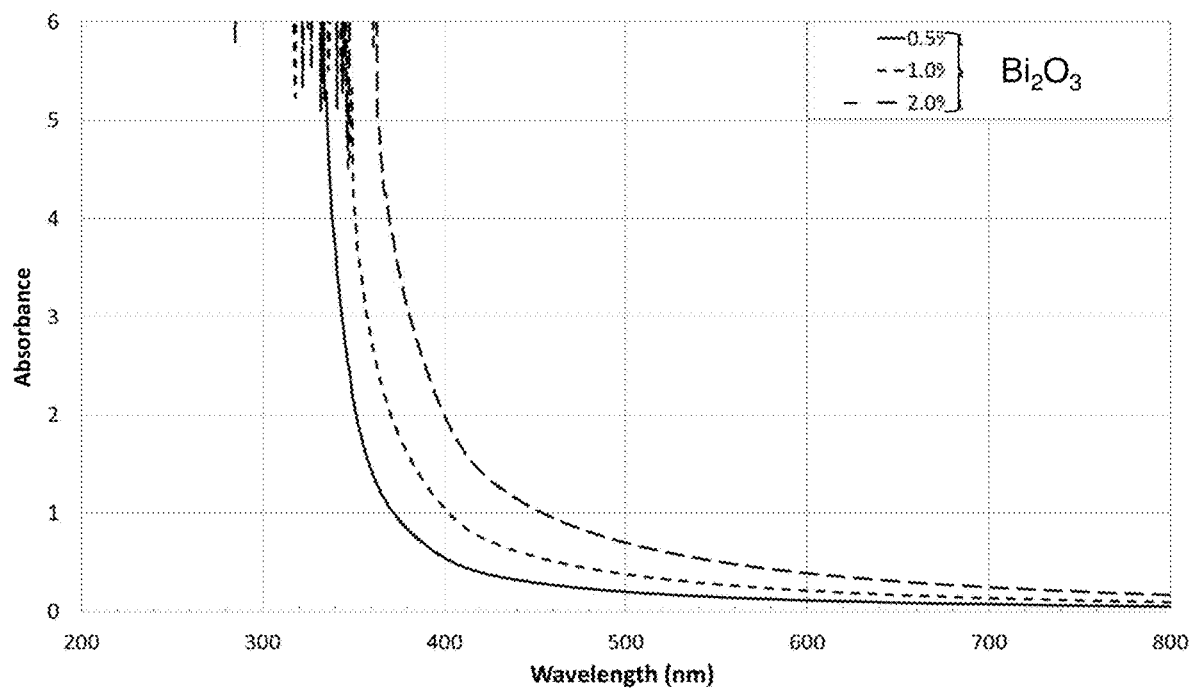
FIG. 4B shows UV absorbance spectra for three different concentrations of bismuth oxide nanoparticles according to the present teachings.
Figure 4C:
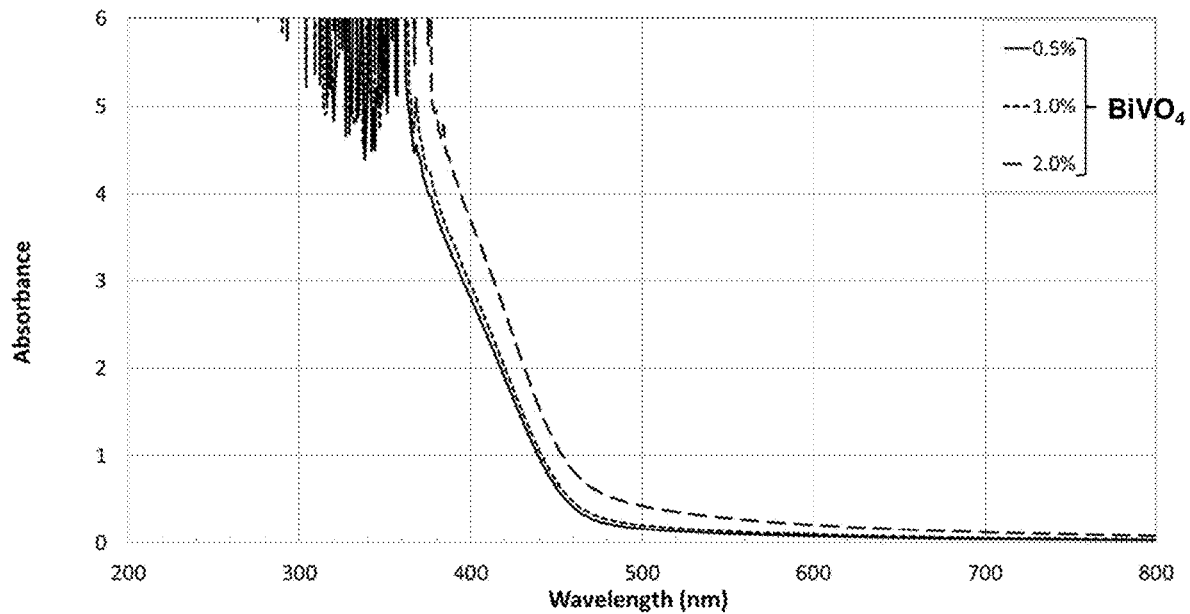
FIG. 4C shows UV absorbance spectra for three different concentrations of bismuth vanadate nanoparticles according to the present teachings.
Figure 4C:
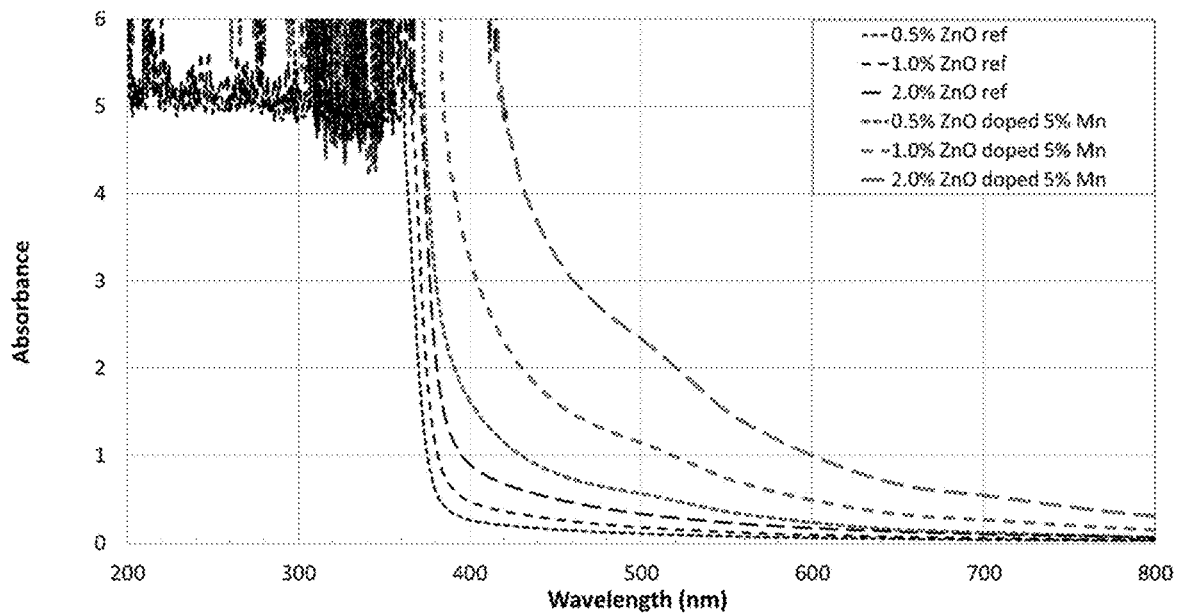

Absorbance of the 5% copper-doped zinc oxide nanoparticles over the wavelength range of 200-800 nm was measured for each concentration using a Cary 300 UV-Vis spectrophotometer with quartz cuvette (10 mm light pathway). Suspensions of undoped zinc oxide at same concentrations served as references. Results are presented in FIG. 4D-B for the 200-800 nm range and in FIG. 4D-C for a close-up view in the 340-500 nm sub-range. As seen in FIG. 4D-B, and better shown in FIG. 4D-C, at each of the tested concentrations, zinc oxide nanoparticles doped with 5% copper showed significantly greater absorbance of UV radiation in the 380-400 nm wavelength range, as compared to the absorbance of undoped zinc oxide nanoparticles at the same concentrations. Absorbance in the 380-400 nm range was found to increase with zinc oxide concentration for the tested concentrations.

Example 4: Comparison of Absorbance of UV Radiation by Nanoparticles of Inorganic UV-Absorbing Agents to that of a Commercially Available Organic Sunscreen Composition Skingard® sunscreen composition by Careline® (Pharmagis, Israel) is a commercially available chemical sunscreen composition. The Skingard® product was burned in a ceramic oven (Vulcan 3-1750) at 500° C. for 5 hours after which the weight percentage of residual solids was found to be very low (0.07%), suggesting that the Skingard® product substantially comprises organic compounds.

An aqueous suspension of 9% (w/w) bismuth oxide nanoparticles of median hydrodynamic diameter (D50 of the number of particles) of about 20 nm and having a $D_N95$ of about 28 nm, a $D_N97.5$ of about 31 nm and a $D_N99$ of about 35 nm was prepared by milling, as described in Example 2. Absorbance over the wavelength range of 200-800 nm was measured for the 9% (w/w) bismuth oxide nanoparticles, for a 9% (w/w) undoped zinc oxide reference and for the Skingard® comparative composition. Absorbance measurements were performed as previously described. Results are presented in FIG. 5A, which shows that absorbance of bismuth oxide in the 380-400 nm wavelength range was greater than that of zinc oxide, and at least equal to that of Skingard®.

An aqueous suspension of 2% (w/w) bismuth vanadate nanoparticles having a $D_N95$ of about 36 nm, a $D_N97.5$ of about 42 nm and a $D_N99$ of about 65 nm, was prepared by milling, as described in Example 2. Absorbance over the wavelength range of 200-800 nm was measured for the 2% (w/w) bismuth vanadate nanoparticles, for a 2% (w/w) zinc oxide reference and for the Skingard® comparative composition. Absorbance measurements were performed as previously described. Results are presented in FIG. 5B, which shows that absorbance of bismuth vanadate in the 380-400 nm wavelength range was greater than that of zinc oxide, and similar to that of Skingard®.

An aqueous suspension of 2% (w/w) zinc oxide nanoparticles doped with either 5% copper or 5% manganese was prepared by milling, as described in Example 2 above, to provide copper-doped zinc oxide nanoparticles having a $D_N95$ of about 27 nm, a $D_N97.5$ of about 31 nm and a $D_N99$ of about 36 nm and manganese-doped zinc oxide nanoparticles having a $D_N95$ of about 33 nm, a $D_N97.5$ of about 37 nm and a $D_N99$ of about 44 nm. Absorbance over the wavelength range of 200-800 nm was measured for the copper-doped and manganese-doped zinc oxide nanoparticles, for a 2% (w/w) undoped zinc oxide reference and for the Skingard® comparative composition. Absorbance measurements were performed as previously described. Results are presented in FIG. 5C, which shows that absorbance of manganese-doped zinc oxide in the 380-400 nm wavelength range was greater than that of zinc oxide, and at least equal to that of Skingard®.

Figure 6:
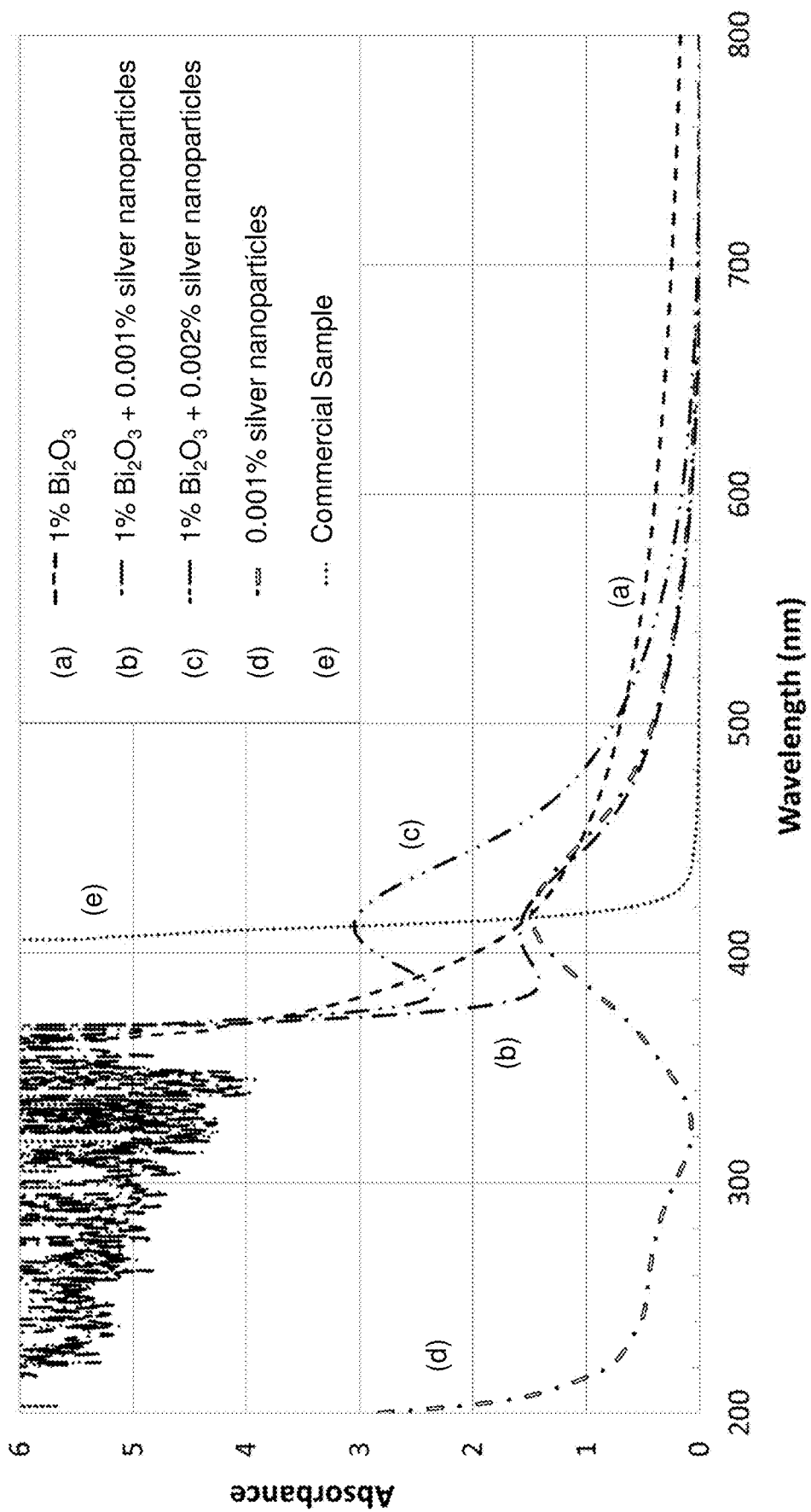
FIG. 6 shows UV absorbance spectra for several embodiments of a sunscreen composition according to embodiments of the invention, each embodiment comprising 1% bismuth oxide with a different concentration of silver nanoparticles, references being included for comparative purposes.

Example 5: Composition Comprising Inorganic UV-Absorbing Agents and Metallic Silver Nanoparticles Silver nanoparticles having a cumulative particle size distribution of hydrodynamic diameter of about 14 nm at D90, about 15 nm at D97.5 and about 17 nm at D99 (in terms of number of particles) are added to a 1% (w/w) suspension in water of a doped or undoped inorganic UV-protective agent of the present teachings, prepared as described above, so that the concentration of silver nanoparticles is either 0.001% or 0.002% (w/w) of the final composition. The absorption of each of the silver particle-containing compositions is measured as described previously, and compared to that of each ingredient separately (i.e. an aqueous suspension of 1% (w/w) of the inorganic UV-protective agent and another of 0.001% silver nanoparticles (w/w)) and to commercially available Skingard® sunscreen composition of Careline®. Results for the experiments using mixtures of bismuth oxide nanoparticles are presented in FIG. 6, addition of 0.002% silver nanoparticles to a suspension of bismuth oxide extended the wavelength at which maximum absorbance was seen from about 380 nm up to about 430 nm.

Example 6: Determination of Critical Wavelength

Figure 5A:
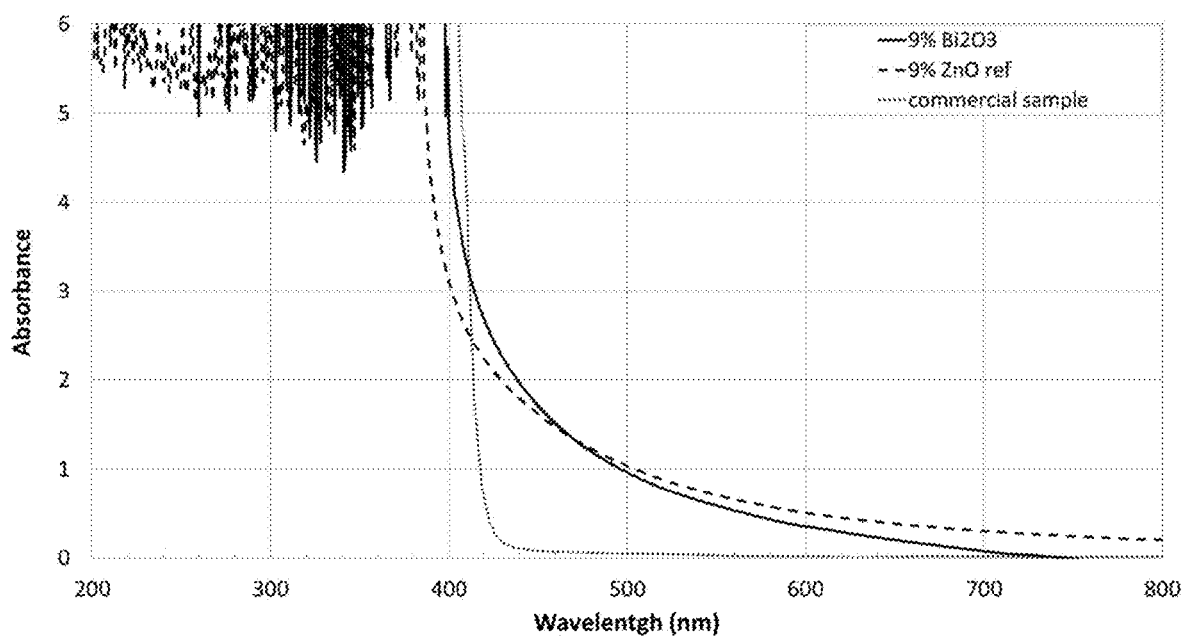
FIG. 5A is a UV absorbance spectrum of a suspension according to an embodiment of the invention comprising 9% bismuth oxide as compared to that of a sunscreen composition comprising 9% undoped zinc oxide and a commercially-available sunscreen composition comprising organic UV-absorbing agents as references.
Figure 5B:
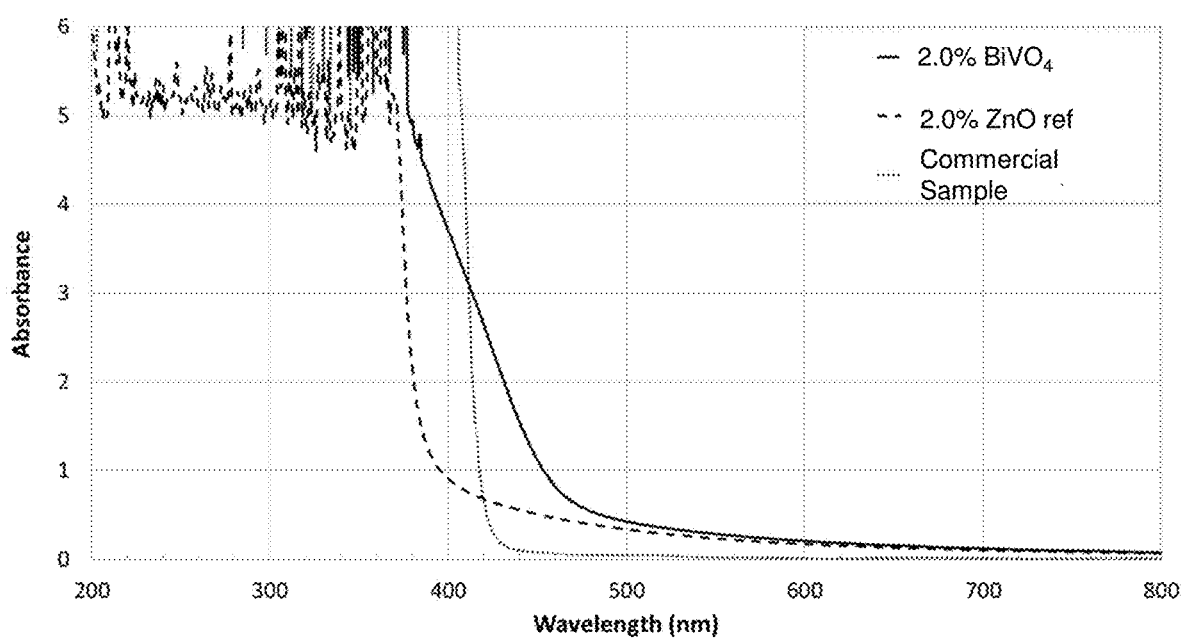
FIG. 5B is a UV absorbance spectrum of a suspension according to an embodiment of the invention comprising 2% bismuth vanadate as compared to that of a sunscreen composition comprising 2% undoped zinc oxide and a commercially-available sunscreen composition comprising organic UV-absorbing agents as references.
Figure 5C:
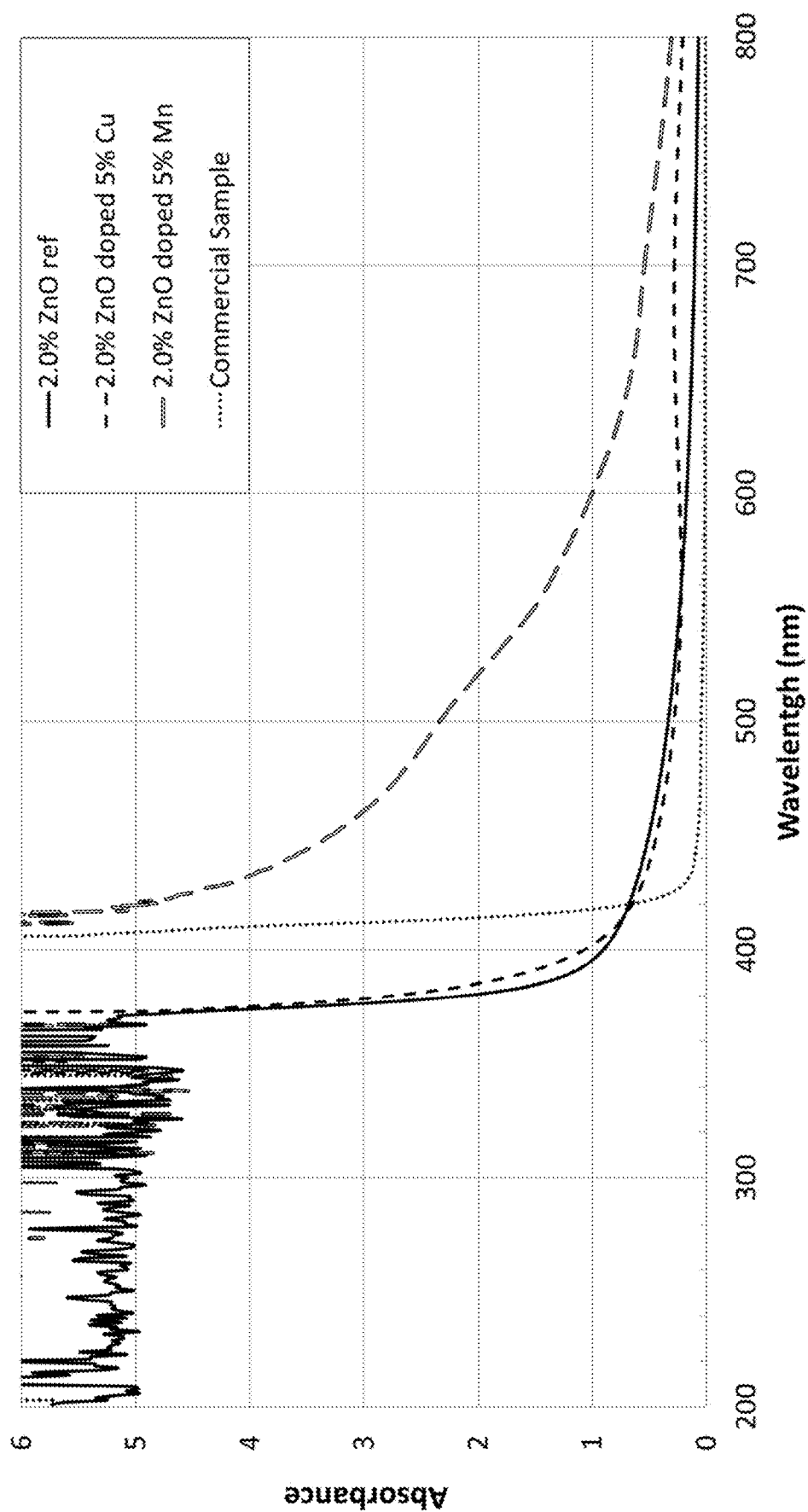
FIG. 5C is a UV absorbance spectrum of a suspension according to an embodiment of the invention comprising 2% (w/w) copper-doped or manganese-doped (5% molar percentage) zinc oxide as compared to that of a sunscreen composition comprising 2% (w/w) undoped zinc oxide and a commercially-available sunscreen composition comprising organic UV-absorbing agents as references.

Based on the absorbance spectra determined above, critical wavelength was calculated for $Bi_2O_3$ ($D_N 95$ ~28 nm) at concentrations 0.5%, 1%, 2% and 9% (w/w); for 1% (w/w) $Bi_2O_3$ with 0.001% or 0.002% (w/w) silver nanoparticles (D95 ~14 nm); for $BiVO_4$ ($D_N 95$ ~36 nm) at concentrations 0.5%, 1%, and 2% (w/w); for zinc oxide at concentrations 0.5%, 1%, 2% and 9% (w/w), doped with 5% copper ($D_N 95$ ~27 nm) or 5% manganese ($D_N 95$ ~33 nm); for undoped ZnO ($D_N 95$ ~39 nm) as reference at concentrations 0.5%, 1%, 2% and 9% (w/w), only the two latter concentrations of the zinc oxide reference being illustrated in FIGS. 5A and 5B; and for the Skingard® product.

Briefly, in order to quantify the breadth of UV protection, the absorbance of the sunscreen composition was integrated from 290 nm to 400 nm the sum reached defining 100% of the total absorbance of the sunscreen in the UV region. The wavelength at which the summed absorbance reaches 90% absorbance was determined as the 'critical wavelength' which provided a measure of the breadth of sunscreen protection.

The critical wavelength $\lambda_c$ was defined according to the following equation:

$$\int_{290}^{\lambda_c} lg[1/T(\lambda)] d\lambda = 0.9 \cdot \int_{290}^{400} lg[1/T(\lambda)] d\lambda$$

wherein:
$\lambda_c$ is the critical wavelength;
$T(\lambda)$ is the mean transmittance for each wavelength; and
$D\lambda$ is the wavelength interval between measurements.

Critical wavelengths as calculated are presented in Table 2 below.

As seen in Table 2, according to the Critical Wavelength Method, $Bi_2O_3$ is classified as providing broad spectrum protection (i.e. has a critical wavelength of greater than 370 nm) at concentrations of from 2%, or at concentration of from 1% in the presence of 0.001% silver nanoparticles.

The density of $Bi_2O_3$ is 8.9 g/cm³, while the density of ZnO is about 5.6 g/cm³. Therefore, the number of particles in each ZnO suspension (at concentrations of 0.5%, 1%, 2% and 9% w/w) is higher than the number of particles in each $Bi_2O_3$ suspension at the same concentration. As the critical wavelengths values of $Bi_2O_3$ were comparable to undoped zinc oxide reference, the physical absorption properties of $Bi_2O_3$ may be considered to be superior to those of ZnO per same amount of particles. As the particle size distribution of the $Bi_2O_3$ particles is comparable to the distribution of the particles of the ZnO reference (see FIG. 2B), such finding is believed to be significant.

Also seen in Table 2, according to the Critical Wavelength Method, $BiVO_4$ is classified as providing broad spectrum protection (i.e. has a critical wavelength of greater than 370 nm) at concentrations of from 0.5%.

The density of $BiVO_4$ is 6.1 g/cm³, while the density of ZnO is about 5.6 g/cm³. Therefore, the number of particles in each ZnO suspension (at concentrations of 0.5%, 1%, and 2% w/w) is higher than the number of particles in each $BiVO_4$ suspension at the same concentration. As the critical wavelengths values of $BiVO_4$ were greater than those of the undoped zinc oxide reference, the physical absorption properties of $BiVO_4$ may be considered to be superior to those of ZnO per same amount of particles. As the particle size distribution of the $BiVO_4$ particles is comparable to the distribution of the particles of the ZnO reference (see FIG. 2C), such finding is believed to be significant.

Also as seen in Table 2, according to the Critical Wavelength Method, doped zinc oxide is classified as providing broad spectrum protection (i.e. has a critical wavelength of greater than 370 nm) at concentrations of from 0.5% (w/w) when the dopant is 5% manganese in molar percentage, or at concentration of from 2% (w/w) when the dopant is 5% copper in molar percentage.

TABLE 2

| Material name and concentration (w/w) | Critical Wavelength (nm) |
| --- | --- |
| 0.5% $Bi_2O_3$ | 349 |
| 1.0% $Bi_2O_3$ | 362 |
| 2.0% $Bi_2O_3$ | 371 |
| 9.0% $Bi_2O_3$ | 389 |
| 1% $Bi_2O_3$ + 0.001% silver nanoparticles | 370 |
| 1% $Bi_2O_3$ + 0.002% silver nanoparticles | 379 |
| 0.5% $BiVO_4$ | 378 |
| 1.0% $BiVO_4$ | 379 |
| 2.0% $BiVO_4$ | 380 |
| 0.5% ZnO doped 5% Cu | 358 |
| 1.0% ZnO doped 5% Cu | 363 |
| 2.0% ZnO doped 5% Cu | 370 |
| 9.0% ZnO doped 5% Cu | 388 |
| 0.5% ZnO doped 5% Mn | 372 |
| 1.0% ZnO doped 5% Mn | 381 |
| 2.0% ZnO doped 5% Mn | 391 |
| 0.5% ref ZnO | 362 |
| 1.0% ref ZnO | 366 |
| 2.0% ref ZnO | 372 |
| 9.0% ref ZnO | 384 |

Example 5: Non-Aqueous Compositions Comprising Bismuth Oxide or Bismuth Vanadate Nanoparticles Powders of bismuth oxide and bismuth vanadate having an average particle size of about 5 μm were size-reduced as described above, subject to the following modifications. The water medium was replaced by an oil carrier, namely $C_{12}$-$C_{15}$ alkyl benzoate (commercially available from Phoenix Chemical as Pelemol® 256), and the water-miscible PAA dispersant was replaced by a vegetable-derived polyester obtained from the homopolymerization of hydroxystearic acid (commercially available from Phoenix Chemicals as Pelemol® PHS-8).

The oil-based slurries were milled as described for the aqueous counterparts. The resulting product was a 10% (w/w) suspension of bismuth oxide or bismuth vanadate nanoparticles in oil, the inorganic solid content being assessed by oven burning as described above.

The oil suspensions of bismuth oxide and bismuth vanadate nanoparticles were diluted in $C_{12}$-$C_{15}$ alkyl benzoate to obtain particle concentrations of 0.5%, 1.0% or 2.0% (w/w), then sonicated for 30 seconds using a Misonix Sonicator tip (Misonix, Inc.) at amplitude 100, 15 W.

The hydrodynamic diameter of the oil-dispersed nanoparticles was determined by Dynamic Light Scattering, using a Zen 3600 Zetasizer from Malvern Instruments Ltd. (Malvern, UK) using the suspension containing 0.5 wt. % nanoparticles.

Figure 7:
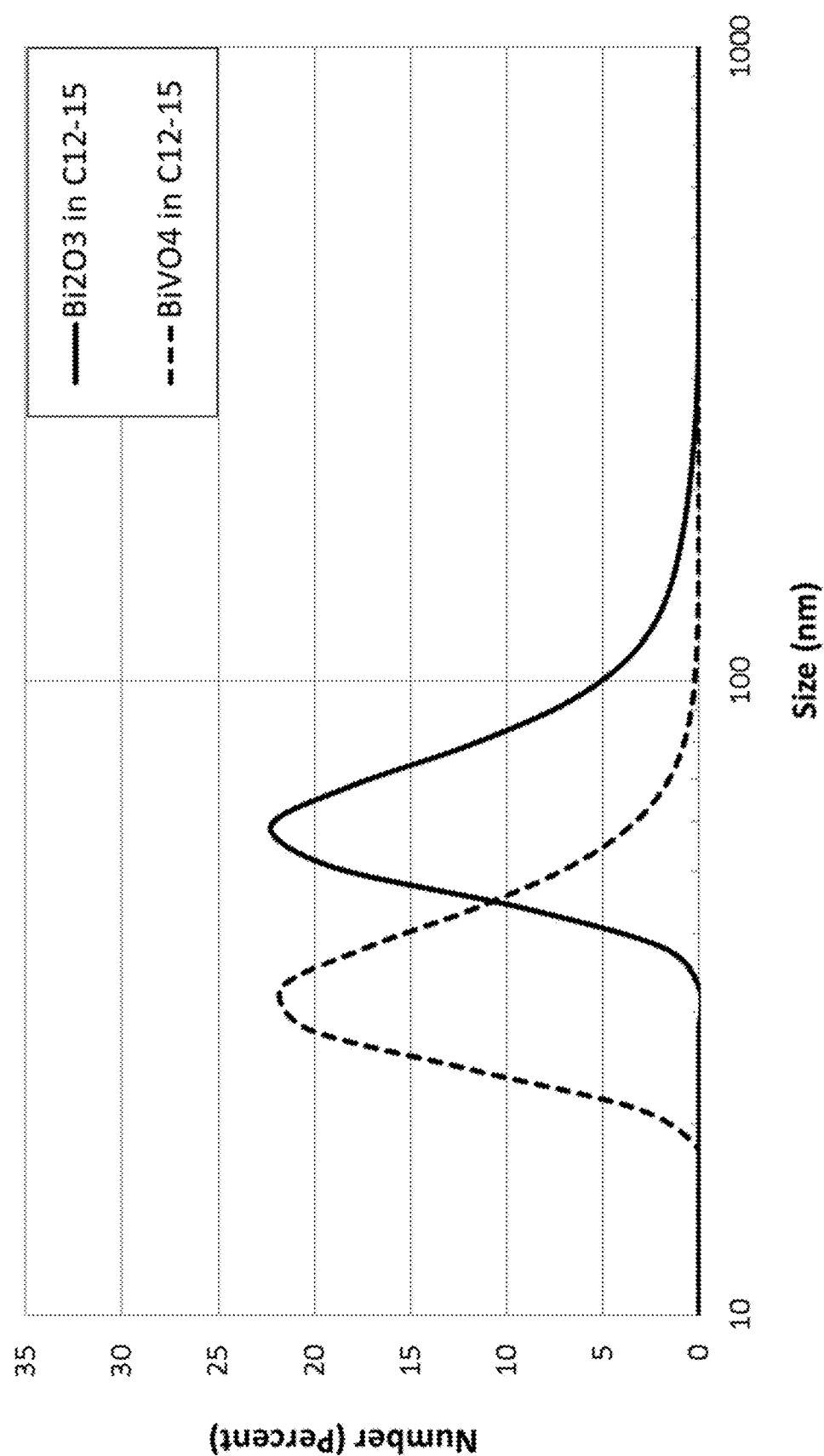
FIG. 7 is a line graph showing the distribution of bismuth oxide and bismuth vanadate nanoparticle sizes used in implementing a specific embodiment of the invention described herein.

Results showing the percentage of the number of bismuth oxide and bismuth vanadate particles having hydrodynamic diameters in the range of 10-1000 nm are presented in FIG. 7, which shows that the majority of bismuth oxide nanoparticles in oil suspension had hydrodynamic diameters in the size range of from about 30 nm and up to about 250 nm, mainly not exceeding 100 nm with a predominant peak around about 60 nm. Specifically, the cumulative particle size distributions for the hydrodynamic diameter of bismuth oxide particles at D95, D97.5 and D99 of the population, analyzed in terms of percentage of number of particles, were found to be about 134 nm, about 167 nm and about 199 nm, respectively.

The majority of bismuth vanadate particles in suspension had hydrodynamic diameters in the size range of from about 18 nm and up to about 100 nm, with a predominant peak around about 34 nm. Specifically, the cumulative particle size distribution for the hydrodynamic diameter of titanium dioxide particles at D95, D97.5 and D99 of the population, analyzed in terms of percentage of number of particles were found to be about 59 nm, about 68 nm and about 82 nm, respectively.

Figure 8:
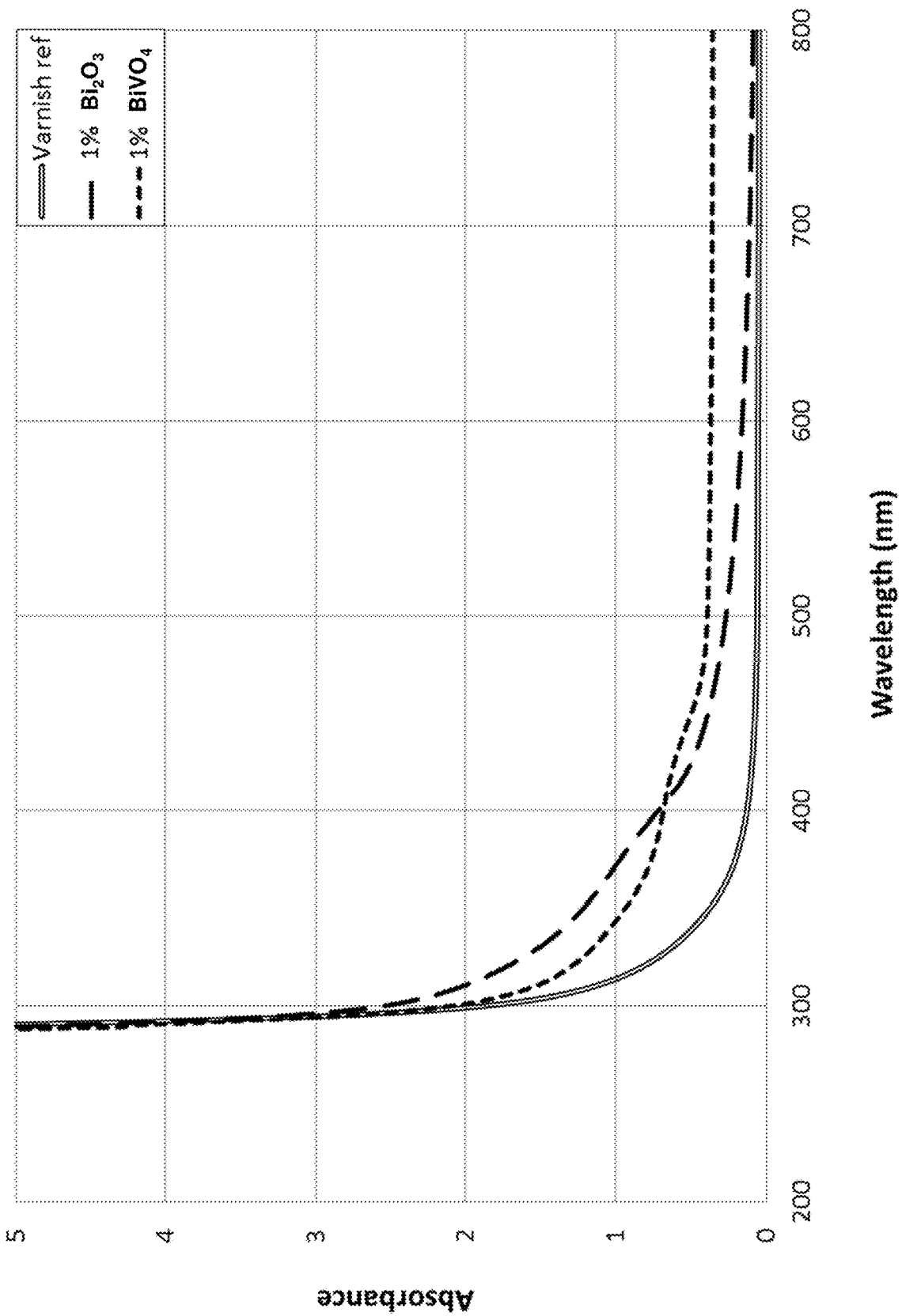
FIG. 8 is a UV absorbance spectrum of lacquer compositions according to embodiments the invention containing either bismuth oxide or bismuth vanadate, as well a lacquer composition without bismuth oxide or bismuth vanadate as a reference for comparative purposes.

The bismuth oxide and bismuth vanadate nanoparticles oil-milled suspensions were also each diluted in a clear wood lacquer (Tambour Clear Glossy Lacquer for Wood No. 8, Cat. No. 149-001) to a particle concentration of 1% by weight of the total lacquer composition. The resulting mixtures were sonicated for 30 seconds using a Misonix Sonicator tip (Misonix, Inc.) at amplitude 100, 15 W. The sonicated lacquer dispersions were applied upon a microscopic glass slide at an initial thickness of about 100 μm (using 100 μm thick spacers and a leveling rod). The lacquer-coated slides were left to dry for at least 12 hours at ambient temperature (circa 23° C.) resulting in a dried layer of sample of about 5 μm. The lacquer devoid of added nanoparticles served as control. Absorbance of the dried layers of lacquer over the wavelength range of 200-800 nm was assessed using a Cary 300 UV-Vis spectrophotometer. Results are shown in FIG. 8, which shows that both bismuth oxide and bismuth vanadate nanoparticles improve the absorbance of the lacquer vehicle over the UV range of interest. The critical wavelength calculated for a 5 μm dried layer of lacquer containing 1 wt. % of bismuth oxide was found to be about 380 nm, while for a similar sample containing 1 wt. % of bismuth vanadate displayed a critical wavelength of about 382 nm. For comparison, the "plain" lacquer control had a critical wavelength of about 360 nm. Such relatively high value is to be expected from such a product aimed, among other things, to protect wood products subjected to external conditions and weather exposures. This study supports the applicability of compounds according to the present teachings for use in non-aqueous carriers and/or on inert objects as well.

Figure 9:
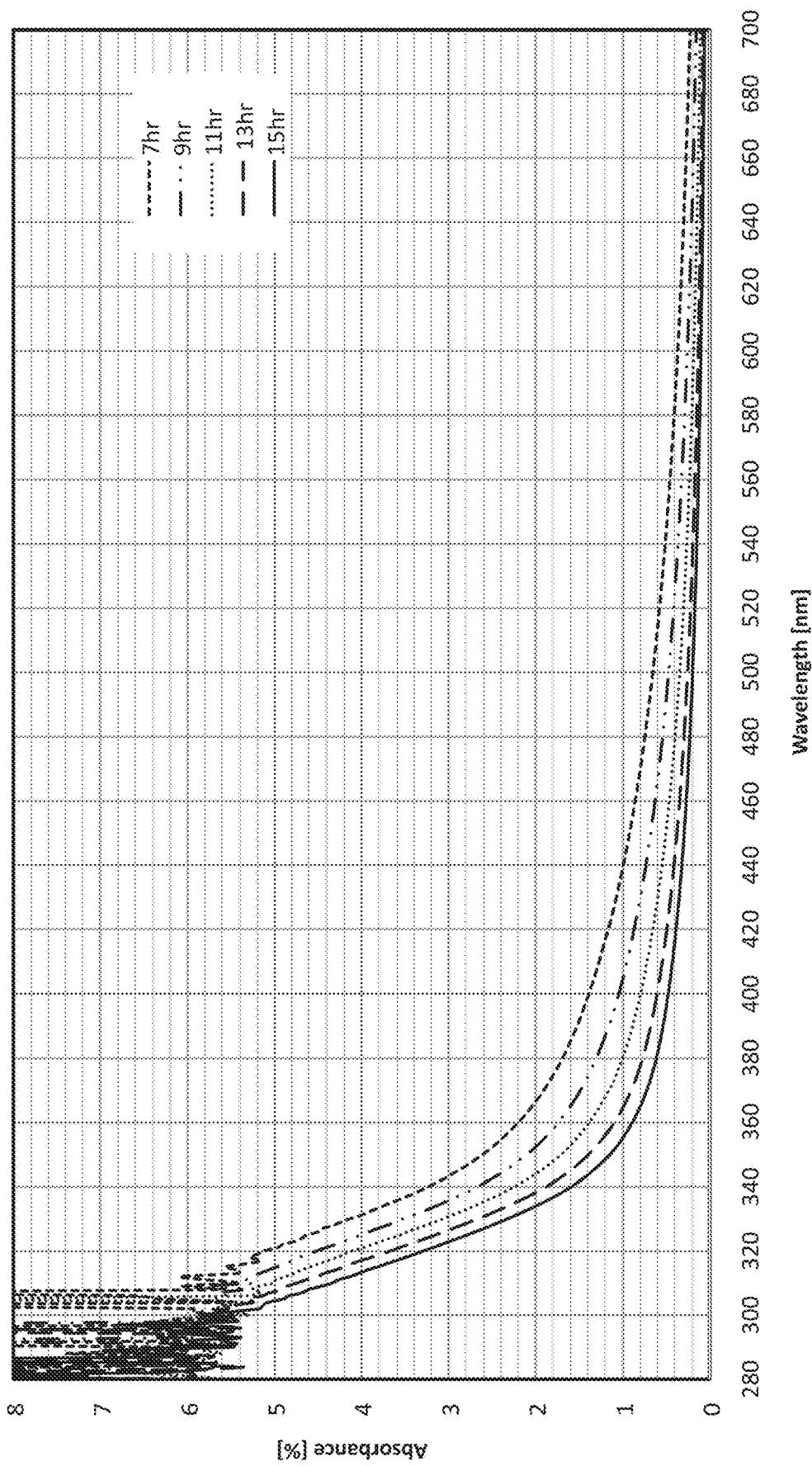
FIG. 9 provides UV absorbance spectra for a composition based on barium titanate, in which the UV absorbance spectra for composition samples are characterized as a function of the milling time of the samples.

FIG. 9 provides UV absorbance spectra for a composition based on barium titanate, in which the UV absorbance spectra for composition samples are characterized as a function of the milling time of the samples. The compositions were prepared substantially as described in Example 2, with samples being removed at various times, for characterization purposes. As milling time is increased (e.g., from 7 hours to 15 hours), it is manifest that the absorption curves are shifted down and to the left, in a monotonic fashion. Thus, for a given wavelength between about 320 nm and 700 nm, the absorbance (in absorbance units AU) exhibited by the sample milled for 15 hours is lower than the sample milled for 13 hours. This trend is exhibited for all samples (milling times of 7, 9, 11, 13, and 15 hours).

Particle size distribution information, including PDI, are provided below as a function of milling time. The values are averaged based on 3 samples per milling time.

| Milling time | $D_v(50)$ Avg. | $D_n(50)$ Avg. | PDI Avg. |
|---|---|---|---|
| 2 hr | 238.7 | 90.1 | 0.181 |
| 4 hr | 175.3 | 81.4 | 0.189 |
| 5 hr | 150.0 | 66.7 | 0.175 |
| 6 hr | 137.3 | 69.7 | 0.162 |
| 7 hr | 136.0 | 72.8 | 0.159 |
| 9 hr | 103.6 | 42.8 | 0.182 |
| 11 hr | 90.1 | 47.5 | 0.186 |
| 13 hr | 80.4 | 43.5 | 0.247 |
| 15 hr | 69.7 | 44.2 | 0.220 |

It will be appreciated that further reduction in size, particularly of the large particles, may be achieved by further milling, using finer milling media, etc. The criticality of the weight ratio of dispersant to inorganic UV-absorbing agents is further elaborated hereinbelow.

The area under curve (AUC) and UV absorbance selectivity data are provided below:

| | AUC(280-400) | AUC(280-700) | UV absorbance selectivity |
|---|---|---|---|
| 7 hr | 469 | 643 | 72.9 |
| 9 hr | 408 | 534 | 76.4 |
| 11 hr | 358 | 451 | 79.5 |
| 13 hr | 341 | 409 | 83.3 |
| 15 hr | 311 | 365 | 85.4 |

Calculation of both the critical wavelength and the UV absorption selectivity may be facilitated by the gridlines provided in the Figure.

It is further observed that the absolute drop in absorbance within the UV range between about 320 and 400 nm is considerably larger than the absolute drop in absorbance within the visible range between about 400 and 700 nm. It would appear that the additional milling time disadvantageously reduces the UV absorbance, and disadvantageously reduces the critical wavelength.

However, the inventors have found that the reduction in UV absorbance within the visible range is appreciable, such that the UV absorbance selectivity may be appreciably improved. Consequently, the formulations of the present invention may be significantly more transparent than identical formulations in which the inorganic UV-absorbing agents (barium titanate and bismuth vanadate) have a larger particle size.

Without wishing to be limited by theory, the inventors believe that the measured UV absorbance within the visible range may actually include a major contribution due to scatter, which may be caused by particles at the high end of the particle size distribution.

The inventors believe that for a given median particle size ($D_N50$), improved efficacy, including a higher UV absorbance selectivity, may be obtained by operating the milling stage so as to obtain a relatively low PDI. This may be achieved by using an excess of dispersant with respect to the inorganic UV-absorbing agents, and by using a dispersant that is particularly efficacious in dispersing the inorganic UV-absorbing agents.

To this end, the weight ratio of dispersant to inorganic UV-absorbing agents may be increased above and beyond the increase required by the additional surface area produced by the size reduction.

All of the above may be coupled with size reduction to a suitably low characteristic particle size, so as to achieve an absorbance curve that provides superior UV absorbance (though not necessarily up to the 400 nm boundary) along with high UV absorbance selectivity, such that the formulation has excellent transparency properties (minute absorbance in the visible range, and relatively little scatter).

CONCLUSIONS

Barium titanate was shown to provide at least equivalent absorbance of ultraviolet radiation in the 280-400 nm range and in particular at the higher end of the range i.e. about 380-400 nm range than that of the known inorganic sunscreen component titanium dioxide. Nanoparticles of barium titanate also provide excellent UV absorbance, while providing a composition which is substantially invisible when applied to the skin.

Bismuth oxide was shown to provide at least equivalent absorbance of ultraviolet radiation in the 280-400 nm range, and in particular at the higher end of the range i.e. about 380-400 nm range than that of the known inorganic sunscreen component zinc oxide. Nanoparticles of bismuth oxide also provide excellent UV absorbance, while providing a composition which is substantially invisible when applied to the skin. Nanoparticles of bismuth oxide thus provide excellent absorption of both UVA and UVB radiation, providing broad-spectrum UV protection (i.e. a composition having a critical wavelength of greater than 370 nm), while providing a composition which is invisible when applied to the skin. Absorption of the UVA and UVB radiation was at least as great as that of the known commercial sunscreen composition.

Bismuth vanadate was shown to provide better absorbance of ultraviolet radiation in the 280-400 nm range and in particular at the higher end of the range i.e. about 380-400 nm range than that of the known inorganic sunscreen component zinc oxide. Nanoparticles of bismuth vanadate also provide excellent absorption of both UVA and UVB radiation, providing broad-spectrum UV protection (i.e. a composition having a critical wavelength of greater than 370 nm), while providing a composition which is invisible when applied to the skin. Absorption of the UVA and UVB radiation was at least as great as that of the known commercial sunscreen composition.

Doped zinc oxide was shown to provide at least equivalent absorbance of ultraviolet radiation in the 280-400 nm range and in particular at the higher end of the range i.e. about 380-400 nm range than that of undoped zinc oxide. Nanoparticles of doped zinc oxide thus provide excellent UV absorption, while providing a composition which is substantially invisible when applied to the skin or hair of a subject. Absorption of the UVA and UVB radiation was at least as great as that of the known commercial sunscreen composition.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

We claim:

1. A UV-protective composition comprising nanoparticles of at least one inorganic UV-absorbing agent selected from the group consisting of (i) barium titanate (BaTiO3) and (ii) bismuth vanadate (BiVO4); and a dispersant associated with said nanoparticles, wherein a weight ratio of said dispersant to said inorganic UV-absorbing agent is within a range of 1:2.5 to 2.5:1, and wherein said dispersant includes a neutralized polyacrylic acid;
wherein said inorganic UV-absorbing agent has a median particle diameter, on a particle number basis (DN50), of at most 80 nm;
wherein a critical wavelength of said inorganic UV-absorbing agent is within a range of 330 to 400 nm;
and wherein a UV absorbance selectivity is defined by $$RAUC = 100\% \cdot (AUC_{280\text{-}400})/(AUC_{280\text{-}700})$$

wherein:
RAUC is said UV absorbance selectivity;
$AUC_{280\text{-}400}$ is a UV-absorbance by the composition or by said inorganic UV-absorbing agent, over a wavelength range of 280 nm to 400 nm; and
$AUC_{280\text{-}700}$ is a UV-absorbance by the composition or by said inorganic UV-absorbing agent, over a wavelength range of 280 nm to 700 nm;
and wherein said UV absorbance selectivity of said inorganic UV-absorbing agent is at least 60%.

2. The UV-protective composition of claim 1, wherein said UV absorbance selectivity of said inorganic UV-absorbing agent is at least 70%.

3. The UV-protective composition of claim 1, wherein said UV absorbance selectivity of said inorganic UV-absorbing agent is at least 75%.

4. The UV-protective composition of claim 1, wherein said inorganic UV-absorbing agent comprises said barium titanate, and wherein said UV absorbance selectivity of said barium titanate is at least 80%.

5. The UV-protective composition of claim 1, wherein a polydispersity index (PDI) of said inorganic UV-absorbing agent is within a range of 0.13 to 0.30.

6. The UV-protective composition of claim 1, wherein said $D_N50$ is within a range of 15 nm to 70 nm.

7. The UV-protective composition of claim 1, wherein said $D_N50$ is within a range of 15 nm to 60 nm.

8. The UV-protective composition of claim 5, wherein said $D_N50$ is within a range of 25 nm to 50 nm.

9. The UV-protective composition of claim 1, wherein said inorganic UV-absorbing agent comprises said bismuth vanadate, and wherein said UV absorbance selectivity of said bismuth vanadate is at least 65%.

10. The UV-protective composition of claim 1, wherein said inorganic UV-absorbing agent comprises said bismuth vanadate, and wherein said UV absorbance selectivity of said bismuth vanadate is at least 70%.

11. The UV-protective composition of claim 1, wherein said weight ratio of said dispersant to said inorganic UV-absorbing agent is within a range of 1:2.0 to 2.0:1.

12. The UV-protective composition of claim 1, wherein at least a portion of said dispersant at least partially envelops said inorganic UV-absorbing agent.

13. The UV-protective composition of claim 1, wherein said critical wavelength of said inorganic UV-absorbing agent is at least 345 nm.

14. The UV-protective composition of claim 1, wherein said critical wavelength of said inorganic UV-absorbing agent is at least 360 nm.

15. A UV-protective composition comprising nanoparticles of at least one inorganic UV-absorbing agent selected from the group consisting of (i) barium titanate (BaTiO3) and (ii) bismuth vanadate (BiVO4), and a dispersant associated with said nanoparticles, wherein a weight ratio of said dispersant to said inorganic UV-absorbing agent is within a range of 1:2.5 to 2.5:1, and wherein said dispersant includes a neutralized polyacrylic acid;

wherein said inorganic UV-absorbing agent has a median particle diameter, on a particle number basis (DN50), of at most 80 nm;

wherein a critical wavelength of said inorganic UV-absorbing agent is within a range of 330 to 400 nm;

wherein an area under the curve formed by UV-absorption of a particular one of said inorganic UV-absorbing agent, as a function of wavelength in a range of 280 nm to 400 nm ($AUC_{280-400}$), is at least 75% of the AUC formed by said particular one of said inorganic UV-absorbing agent, at the same concentration, in a range of 280 nm to 700 nm ($AUC_{280-700}$), and wherein an overall polydispersity index (PDI) of said inorganic UV-absorbing agent is within a range of 0.13 to 0.30.

16. The UV-protective composition of claim 15, wherein a weight ratio of said dispersant to said inorganic UV-absorbing agent is within a range of 1:2 to 2:1.

17. A UV-protective composition comprising nanoparticles of an inorganic UV-absorbing agent selected from the group consisting of (i) barium titanate (BaTiO3) and (ii) bismuth vanadate (BiVO4), and a dispersant associated with said nanoparticles, wherein a weight ratio of said dispersant to said inorganic UV-absorbing agent is within a range of 1:2.5 to 2.5:1, and wherein said dispersant includes a neutralized polyacrylic acid;

wherein said inorganic UV-absorbing agent has a median particle diameter, on a particle number basis ($DN_{50}$), of at most 80 nm;

and wherein a critical wavelength of said inorganic UV-absorbing agent is within a range of 330 to 400 nm.

18. The UV-protective composition of claim 17, wherein said weight ratio of said dispersant to said inorganic UV-absorbing agent is within a range of 1:2.0 to 2.0:1.

* * * * *